United States Patent
Shalon et al.

(10) Patent No.: US 10,604,954 B2
(45) Date of Patent: Mar. 31, 2020

(54) POOL AND SPA WATER QUALITY CONTROL SYSTEM AND METHOD

(71) Applicant: WATERGURU INC., Palo Alto, CA (US)

(72) Inventors: Tadmor Shalon, Palo Alto, CA (US); Richard A. Falk, San Rafael, CA (US)

(73) Assignee: WATERGURU INC., Palo Alto, CA (US)

( * ) Notice: Subject to any disclaimer, the term of this patent is extended or adjusted under 35 U.S.C. 154(b) by 84 days.

(21) Appl. No.: 15/569,852

(22) PCT Filed: Apr. 26, 2016

(86) PCT No.: PCT/US2016/029293
§ 371 (c)(1),
(2) Date: Oct. 27, 2017

(87) PCT Pub. No.: WO2016/176169
PCT Pub. Date: Nov. 3, 2016

(65) Prior Publication Data
US 2018/0112430 A1 Apr. 26, 2018

Related U.S. Application Data

(60) Provisional application No. 62/293,167, filed on Feb. 9, 2016, provisional application No. 62/153,373, filed on Apr. 27, 2015.

(51) Int. Cl.
*E04H 4/12* (2006.01)
*G01N 33/18* (2006.01)
(Continued)

(52) U.S. Cl.
CPC ........... *E04H 4/1281* (2013.01); *C02F 1/008* (2013.01); *C02F 1/685* (2013.01); *C02F 1/76* (2013.01);
(Continued)

(58) Field of Classification Search
None
See application file for complete search history.

(56) References Cited

U.S. PATENT DOCUMENTS

| | | | |
|---|---|---|---|
| 2,758,710 | A | 8/1956 | Arens |
| 2,889,958 | A | 6/1959 | Ekenstam et al. |

(Continued)

FOREIGN PATENT DOCUMENTS

| | | |
|---|---|---|
| DE | 3932400 A1 | 4/1991 |
| JP | 3089916 B2 | 7/2000 |

OTHER PUBLICATIONS

Blue I Water Technologies; Prizma; (http://www.blueitechnologies.com/products/prizma/); product page; 1 page; Accessed from the WayBackMachine on Jan. 19, 2018.

(Continued)

*Primary Examiner* — Richard C Gurtowski
(74) *Attorney, Agent, or Firm* — Shay Glenn LLP

(57) ABSTRACT

A water quality management system for a water installation containing water. In some embodiments, the system includes a water quality measurement module adapted to monitor the water quality of the water in the water installation and to send water quality information to a controller; a chemical dispensing module adapted to dispense chemicals directly into the water installation in response to signals from the controller; and a communication mechanism configured to provide communication among the controller, the water quality measurement module, the chemical dispensing module and a user.

30 Claims, 15 Drawing Sheets

(51) Int. Cl.
*C02F 1/68* (2006.01)
*C02F 1/76* (2006.01)
*C02F 1/00* (2006.01)
C02F 1/78 (2006.01)
C02F 1/467 (2006.01)
C02F 1/32 (2006.01)
C02F 103/42 (2006.01)

(52) U.S. Cl.
CPC ............... *G01N 33/18* (2013.01); *C02F 1/32* (2013.01); *C02F 1/4674* (2013.01); *C02F 1/78* (2013.01); *C02F 2103/42* (2013.01); *C02F 2201/006* (2013.01); *C02F 2209/005* (2013.01); *C02F 2209/008* (2013.01); *C02F 2209/02* (2013.01); *C02F 2209/06* (2013.01); *C02F 2209/11* (2013.01); *C02F 2209/29* (2013.01); *C02F 2303/04* (2013.01)

(56) References Cited

U.S. PATENT DOCUMENTS

| | | | |
|---|---|---|---|
| 3,638,833 A | 2/1972 | Lucas | |
| D233,887 S | 12/1974 | Bower et al. | |
| 4,056,470 A | 11/1977 | Carpenter | |
| 4,129,230 A | 12/1978 | Billett et al. | |
| 4,389,325 A | 6/1983 | Eng et al. | |
| D273,977 S | 5/1984 | Burrows | |
| 4,552,605 A | 11/1985 | Itoh et al. | |
| 4,769,137 A | 9/1988 | Powell, Jr. | |
| 4,780,197 A | 10/1988 | Schuman | |
| 4,825,528 A | 5/1989 | Nicholson et al. | |
| D307,460 S | 4/1990 | Bradford et al. | |
| 4,917,868 A | 4/1990 | Alexander et al. | |
| 5,019,250 A | 5/1991 | Lorenzen | |
| D358,868 S | 5/1995 | Hembree et al. | |
| 5,476,116 A | 12/1995 | Price et al. | |
| 5,614,528 A | 3/1997 | Jones et al. | |
| 5,662,795 A | 9/1997 | Pickens et al. | |
| 5,804,080 A | 9/1998 | Klingenberger | |
| 5,851,406 A | 12/1998 | Jones et al. | |
| 5,985,155 A | 11/1999 | Maitland | |
| 6,113,858 A | 9/2000 | Tang et al. | |
| 6,200,487 B1 | 3/2001 | Denkewicz et al. | |
| 6,238,553 B1 | 5/2001 | Lin | |
| 6,343,697 B1 | 2/2002 | Hausdorf et al. | |
| 6,387,251 B1 | 5/2002 | Marsiglietti et al. | |
| 6,567,166 B2 | 5/2003 | Ottens et al. | |
| 6,583,880 B2 | 6/2003 | Berstis | |
| 6,894,778 B2 | 5/2005 | Palumbo et al. | |
| D535,352 S | 1/2007 | Verdon | |
| 7,292,898 B2 | 11/2007 | Clark et al. | |
| 7,409,853 B2 | 8/2008 | Biberger | |
| D578,179 S | 10/2008 | Verdon | |
| 7,469,519 B2 | 12/2008 | Barthel et al. | |
| 7,544,289 B2 | 6/2009 | Straka et al. | |
| 7,745,517 B2 | 6/2010 | Vicari et al. | |
| D623,719 S | 9/2010 | Lees | |
| 8,007,664 B2 | 8/2011 | Reed et al. | |
| 8,133,398 B2 | 3/2012 | King et al. | |
| 8,197,755 B2 | 6/2012 | Tsur | |
| 8,309,509 B2 | 11/2012 | Bartelme et al. | |
| 8,345,248 B2 | 1/2013 | Hong et al. | |
| 8,404,117 B1 | 3/2013 | Steinbrueck et al. | |
| D687,512 S | 8/2013 | Cullimore | |
| D692,524 S | 10/2013 | Ziser | |
| 8,797,523 B2 | 8/2014 | Clark | |
| 8,968,660 B2 | 3/2015 | Davis et al. | |
| D730,484 S | 5/2015 | Kim | |
| 9,034,193 B2 | 5/2015 | Shalon et al. | |
| D742,997 S | 11/2015 | Sgroi | |
| D781,733 S | 3/2017 | Fernandes | |
| D807,985 S | 1/2018 | Shalon et al. | |
| 2001/0045380 A1 | 11/2001 | Khan | |
| 2002/0056689 A1 | 5/2002 | Shim et al. | |
| 2004/0055969 A1* | 3/2004 | Barnes | C02F 1/008 210/760 |
| 2006/0110292 A1* | 5/2006 | Deverse | G01F 23/292 422/68.1 |
| 2007/0039898 A1* | 2/2007 | Dee | B01J 7/02 422/129 |
| 2007/0094817 A1 | 5/2007 | Stoltz et al. | |
| 2007/0138109 A1 | 6/2007 | Tufano et al. | |
| 2008/0008848 A1 | 1/2008 | Dick et al. | |
| 2008/0021685 A1 | 1/2008 | Emery et al. | |
| 2008/0094235 A1 | 4/2008 | Brochu et al. | |
| 2008/0311898 A1 | 12/2008 | Benco et al. | |
| 2009/0218296 A1 | 9/2009 | King et al. | |
| 2011/0139727 A1 | 6/2011 | Hui | |
| 2011/0253638 A1* | 10/2011 | Easland | C02F 1/004 210/745 |
| 2013/0168327 A1 | 7/2013 | Clark | |
| 2013/0313204 A1* | 11/2013 | Shalon | G01N 33/18 210/744 |
| 2014/0259612 A1 | 9/2014 | Bauckman et al. | |
| 2014/0299526 A1 | 10/2014 | Mastio | |
| 2015/0143785 A1 | 5/2015 | Sun | |
| 2015/0218835 A1 | 8/2015 | Shalon | |
| 2017/0092096 A1 | 3/2017 | Fernandes et al. | |

OTHER PUBLICATIONS

Bullock; Disinfection of swimming pool water; PhD Thesis; Chapter 5 Material and Methods; pp. 60-79; Cranfield University; Oct. 2003.

OnBalance; The role of CO2 in pool water; 5 pages; Jan. 2006; (retrieved from the internet: http://www.anotherperfectpoolnews.com/wp-content/uploa;ds/Tech_Talk/onbalance_ks_co2inwater.pdf).

Wojtowicz; Chemistry of nitrogen compounds in swimming pool water;JSPSI; 4(1); pp. 30-40; Jan. 2004.

* cited by examiner

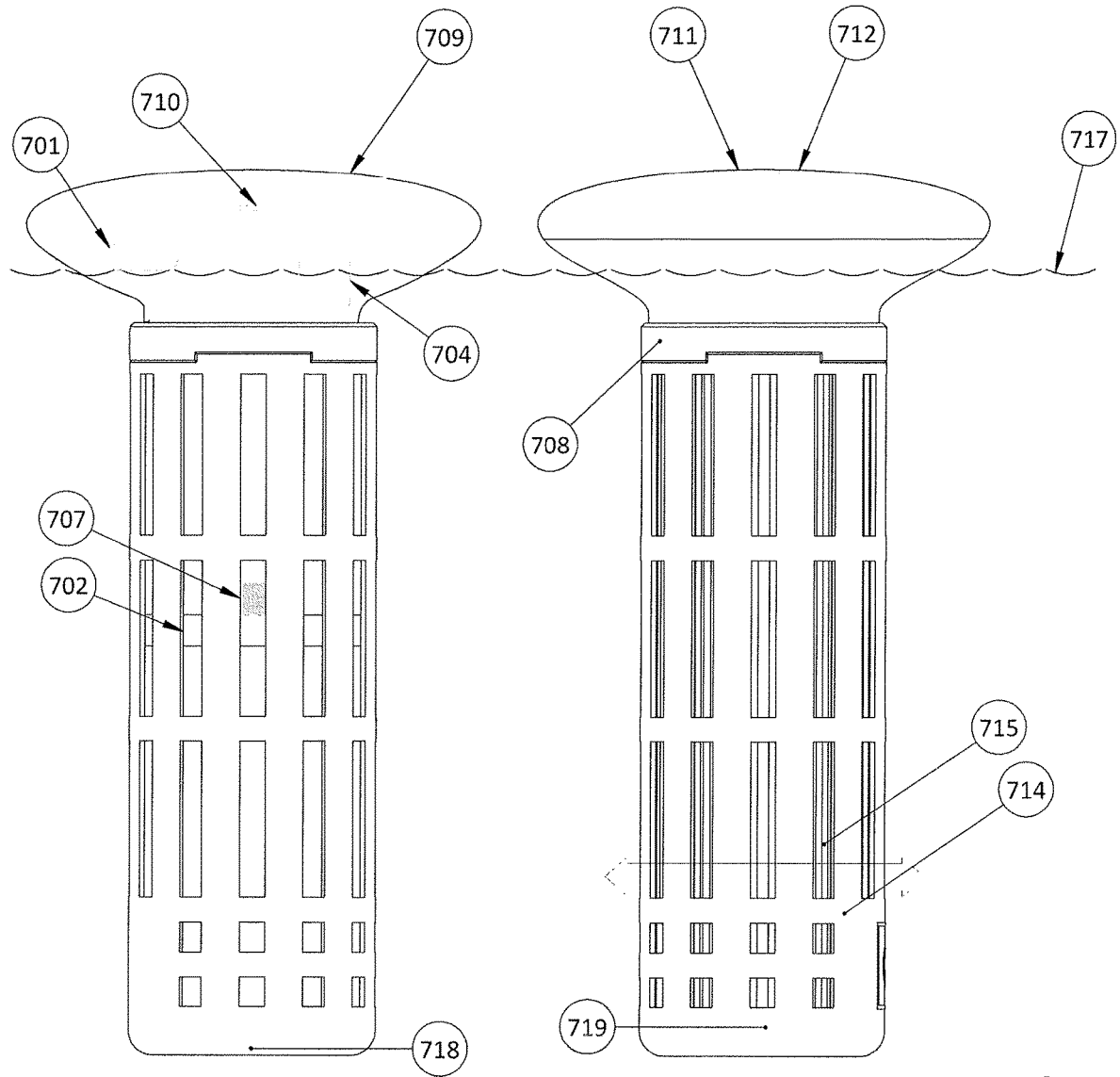
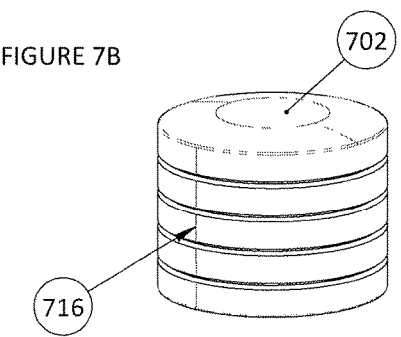
FIGURE 7A   FIGURE 7B   FIGURE 7C

POOL AND SPA WATER QUALITY CONTROL SYSTEM AND METHOD

CROSS REFERENCE TO RELATED APPLICATIONS

This application claims the benefit of U.S. Patent Application No. 62/153,373, filed Apr. 27, 2015, and U.S. Patent Application No. 62/293,167, filed Feb. 9, 2016, each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

The present invention relates to an affordable, modular, and convenient system for homeowners to deploy in their pools or spas in order to optimally maintain the water quality in a safe and responsible way while minimizing use of chemicals and energy.

BACKGROUND

Nearly 15 million US homeowners struggle to optimally control the quality of the water in their pools. (As used herein, "pools" includes spas.) The water is affected by environmental factors such as sunlight, wind, pollen, debris, rain and human factors such as skin bacteria, sweat and urine. Most homeowners or their hired pool service make adjustments on a weekly basis at best. In order to deal with changing conditions, most users overdose their pools with circulating disinfectants, resulting in harsh water that attacks skin, hair and bathing suits, and often requiring additional chemicals to maintain pH. Water chemistry parameters are mutually dependent where free chlorine ("FC") requires a narrow pH range in order to effectively oxidize organic matter and purify the water. If not enough effective disinfectant is present, nutrients in the pool can cause an algae bloom requiring further expensive chemicals and environmentally damaging water change often in excess of 15,000 gallons. This results in over $2.6 billion spent each year in the US by consumers on pool chemicals such as disinfectants, water balance adjusters (for pH, total alkalinity, calcium hardness, and cyanuric acid), algaecides, clarifiers, flocculants, and enzymes which need to be manually administered to pools. Since the popularization of back yard pools in over 15% of all households, no automatic, easy to deploy, cost effective systems have been commercially available to address these needs.

According to the US Department of Energy, the average pool requires 1,500 kWh per year in order to operate its filtration and circulation pumps. Many pool pumps run on a timer that is not responsive to actual filtration need. Saltwater chlorine generators also require significant power and maintenance and are also run on a timer that is not responsive to the actual need of disinfectant in the pools.

Nearly 90% of pool owners in the US maintain their own pools and spas and are not able or willing to make significant investment in installing new equipment requiring plumbing or electrical connections.

Several partial solutions have been offered to the consumer. Manual colorimetric test strips exist that indicate the state of chemicals in the pool water, but those must be applied manually, read on multi-colored comparison charts, and translated to the correct balancing mixture of chemicals needed. It is difficult for the user to connect these weekly measurements and compute the dynamic trajectory of pool water and the required corrective action. This results in over or under correction both of which can be very expensive.

There exist some automation systems for the residential pool market (e.g., the Hayward Sense and Dispense® system). These systems are costly to install and costly to maintain. In addition, they require a disruption of existing plumbing. These systems control only for chlorine and pH and have oxidation-reduction potential (ORP) sensors with a sensitive platinum electrode and pH sensors with a sensitive glass bulb, both of which need regular maintenance for calibration and cleaning.

Dosing disinfectant using tricholoroisocyanuric acid ("trichlor") pucks eluting chlorine from a floating dispenser are the most common. Most users do not bother to manually adjust the dispensing rate in response to pool chlorine demand, however. An inline chlorinator/feeder also uses trichlor pucks, but its dispensing rate is also rarely manually adjusted. Both trichlor dispensing systems require users to handle a hazardous chemical oxidizing puck when these dispensers have to be replenished. Saltwater chlorine generators work on timers that also are rarely manually adjusted based on chlorine demand.

Balancing the pH, alkalinity, and calcium levels of the pool water requires additional measurements, calculations and manual administration of chemicals.

It should be further appreciated that all the processes affecting pool water chemistry mentioned above are not linear, yet users routinely attempt to control them with step adjustments such as adding a fixed amount of chemicals, or changing the setting on a chlorine dispenser, pump timer, etc. subject to infrequent measurement, typically once per week at best. This approach inevitably results in suboptimal adjustments. The present invention describes a modular battery operated system that may be easily deployed one module at a time to deal with the tedious aspects of pool maintenance and relieves the user from these manual tasks and makes repeated measurements and optimized dynamic dosing to keep pool water in ideal condition.

It should be further appreciated that pool service personnel currently use fixed schedules and routes resulting in either visiting pools on their route too frequently or too infrequently often involving considerable driving time and expense. The present invention automatically takes care of most maintenance issues, advises the service center of pool conditions and often proactively reports service issues before they become problems, thereby allowing pool service personnel to perform their work more efficiently by minimizing truck rolls and optimizing routing based on actual service need.

It should be further appreciated that any man-made body of water may require chemical monitoring and adjustment. Cooling towers have to be routinely maintained with sanitizer to avoid bacteria growth that can lead to Legionnaires' disease. In addition to cooling towers, hot tubs, fountains, koi ponds, containment ponds and other open or closed water systems could benefit from one or more of the modules described herein each of which is of low cost, requiring no complex calibration or cleaning, and all but one (the pump control module) are easily added to the pool by the pool owner without need for professional installation.

Colorimetric strips (e.g., Hach Aquachek®, ITS Sensafe®, LaMotte Insta-TEST®) have been available for decades and are the most popular means for analyzing the key analytes in pool water such as FC, pH, alkalinity, and hardness. These pad strips must be manually dipped in the water and the color of the pads compared to a standard chart to read the analyte level. The pad strips must be kept in a sealed container so they do not degrade due to exposure to moisture in the form of liquid water or water vapor present in humid air.

Electronic probes for measuring pH and ORP (which is related to, but not a direct measurement of FC) have been available in commercial systems, but these probes are prone to degradation and calibration drift. While some of these systems simply provide open loop monitoring, others control the dispensing of chemicals based on monitored parameters, such as in U.S. Pat. No. 8,797,523.

Automated pool chemical sensing technology suffers from certain drawbacks. For example, systems have been proposed to sequentially expose pads to pool water as described in U.S. Pat. Nos. 6,113,858 and 8,197,755 or as demonstrated by the Blue I Water Technologies PRIZMA® system (http://www.blueitechnologies.com/products/prizma/), but they do not provide for a way to prevent moisture degradation to the analyte pads or the ability to keep them in the pool water prior to use.

In addition to water chemical monitoring, turbidity monitors have been used to control water circulation pumps in pools, such as described in US Publ. No. 2011/0253638. Circulating water pumps have also been controlled based on pool usage, as described in U.S. Pat. No. 5,804,080.

SUMMARY OF THE DISCLOSURE

One aspect of the invention provides a water quality management system for a water installation containing water. In some embodiments, the system includes a water quality measurement module adapted to monitor the water quality of the water in the water installation and to send water quality information to a controller; a chemical dispensing module adapted to dispense chemicals directly into the water installation in response to signals from the controller; and a communication mechanism configured to provide communication among the controller, the water quality measurement module, the chemical dispensing module and a user.

In some embodiments, the water quality measurement module may be adapted to float in the water. Alternatively or additionally, the water quality measurement module may have a plurality of colorimetric test pads, each test pad enclosed in a water and vapor-proof barrier, a sensor adapted to sense a color change in a test pad and a motor adapted to advance a test pad into the water and to breach the barrier to permit water to reach the test pad.

In any of the preceding embodiments, the water quality measurement module may include a water temperature sensor, the controller being configured to adjust chemical dispensing based on a water temperature signal from the water temperature sensor.

In any of the preceding embodiments, the water quality measurement module may include an air temperature sensor, the controller being configured to adjust chemical dispensing based on an air temperature signal from the air temperature sensor.

In any of the preceding embodiments, the water quality measurement module may include a hydrophone, the controller being configured to adjust chemical dispensing based on a sound signal from the hydrophone.

In any of the preceding embodiments, the water quality measurement module may include a water turbidity sensor, the controller being configured to adjust operation of a water pump based on a turbidity signal from the water turbidity sensor.

In any of the preceding embodiments, the water quality measurement module may include an air humidity sensor, the controller being configured to adjust chemical dispensing based on a humidity signal from the humidity sensor.

In any of the preceding embodiments, the water quality measurement module may include an accelerometer.

In any of the preceding embodiments, the chemical dispensing module may be adapted to float in the water.

In any of the preceding embodiments, the chemical dispensing module may be adapted to maintain orientation and buoyancy as chemicals are dispensed.

In any of the preceding embodiments, the chemical dispensing module may include a collapsible bladder containing a chemical to be dispensed into the water. In such embodiments, the system may also have a chemical port communicating with the bladder and adapted to be underwater.

In any of the preceding embodiments, the system may include a vent adapted to vent gas generated by the chemicals.

In any of the preceding embodiments, the chemical dispensing module may include a quantity of the chemicals enclosed in an water-dissolvable package and disposed in a chemical chamber.

In any of the preceding embodiments, the chemical dispensing module may include a compartment arranged and configured to trap gases released by the chemicals. In some such embodiments, the controller may be configured to activate an opening in the compartment to release the gases.

In any of the preceding embodiments, the chemical dispensing module may include a sensor adapted to sense depletion of the chemical in the chemical dispensing module.

In any of the preceding embodiments, the chemicals may be disposed in doses sealed in waterproof packets, the chemical dispensing module including a motor configured to release a dose of chemicals from a packet.

In any of the preceding embodiments, the system may also include a pump module adapted to control pumping of the water in response to signals from the controller.

Another aspect of the invention provides a water quality measurement apparatus adapted to monitor water quality of a water installation. In some embodiments, the water quality measurement apparatus including a plurality of colorimetric test pads, each test pad enclosed in a water and vapor-proof barrier film; a sensor adapted to sense a color change in a test pad; and a motor adapted to advance a test pad and to breach the barrier to permit water to reach the test pad.

In some embodiments, the water quality measurement apparatus is adapted to float in the water.

In any of the preceding embodiments, the water quality measurement apparatus may include a battery adapted to provide power to the motor.

In any of the preceding embodiments, the water quality measurement apparatus may include a communication mechanism configured to provide communication with other water installation components and/or the Internet.

In any of the preceding embodiments, the water quality measurement apparatus may include a sensor adapted to sense a water parameter, the apparatus being adapted to determine water installation chemical dosing based on information from the sensor and/or from the Internet.

Yet another aspect of the invention provides a chemical sanitizer dispensing apparatus adapted to dispense chemical sanitizer into a water installation. In some embodiments, the apparatus has a housing adapted to extend into water in the water installation; a chemical compartment in the housing and containing sanitizer chemicals; a port extending between the compartment and an exterior portion of the housing; a shutter movable between a first position blocking the port and a second position exposing the port; and a motor adapted to move the shutter between the first and second positions.

In some embodiments, the housing may be adapted to float in the water.

In any of the preceding embodiments, the chemical sanitizer dispensing apparatus may include a battery adapted to provide power to the motor to move the shutter.

In any of the preceding embodiments, the chemical sanitizer dispensing apparatus may include a communication mechanism configured to provide communication with other water installation components and/or the Internet.

In any of the preceding embodiments, the chemical sanitizer dispensing apparatus may include a controller adapted receive information pertaining to water installation pump operation and/or temperature information to determine port exposure times for exposing sanitizer chemical to the water.

In any of the preceding embodiments, the chemical sanitizer dispensing apparatus may include a water dissolving film surrounding the sanitizer chemicals.

In any of the preceding embodiments, the chemical sanitizer dispensing apparatus may include a controller adapted to receive information about water installation use and a vent mechanism adapted to vent gas generated by the sanitizer chemicals when the water installation is not in use.

Still another aspect of the invention provides a chemical dispensing apparatus adapted to dispense a chemical into a water installation. In some embodiments, the chemical dispensing apparatus includes a plurality of chemical packets each arranged in a strip and packaged in a barrier film, each packet containing a dose of chemical; and a packet opening mechanism adapted to dispense a dose of chemical within a packet into the water.

In some embodiments, the chemical dispensing apparatus includes a housing adapted to float in the water installation, the housing supporting the strip and the packet opening mechanism.

In any of the preceding embodiments, the packet opening mechanism may include a battery and a battery-operated motor.

In any of the preceding embodiments, the chemical dispensing apparatus may include a communication mechanism configured to provide communication with other water installation components and/or the Internet.

Yet another aspect of the invention provides a chemical dispensing apparatus adapted to dispense a chemical into a water installation. In some embodiment, the chemical dispensing apparatus includes a movable platform adapted to support a dissolvable chemical beneath the surface of water in the water installation; a reservoir sealable from the water in the water installation; and a motor adapted to move the platform to a position in which the dissolvable chemical is inside the reservoir.

In some embodiments, the chemical dispensing apparatus also includes a housing extending below the reservoir, the housing containing at least one opening, the platform being movable between a position in which the dissolvable chemical communicates with the opening and the position in which the dissolvable chemical is inside the reservoir.

Still another aspect of the invention provides a chemical dispensing apparatus adapted to dispense a chemical into a water installation. In some embodiments, the chemical dispensing apparatus includes a housing adapted to float in the water installation; a collapsible bladder adapted to contain the chemical; and a discharge port adapted to discharge the chemical from the bladder.

Yet another aspect of the invention provides a pump control apparatus adapted to control a water circulation pump in a water installation. In some embodiments, the pump control apparatus includes an electrical current and/or sensor adapted to generate sensor signal; and a controller adapted to determine at least one of pump load and filtration system service condition from the sensor signal.

In some embodiments, the pump control apparatus also includes a communication mechanism configured to provide communication with other water installation components and the Internet to optimize pump operation. The pump control apparatus may be further adapted to operate the pump in response to a water turbidity measurement.

BRIEF DESCRIPTION OF THE DRAWINGS

FIG. 1A is a side view. FIG. 1B is a top view. FIG. 1C is a perspective view.

FIGS. 7A-C show aspects of a chemical sanitizer dispensing apparatus according to an aspect of the invention.

DETAILED DESCRIPTION

The invention provides modular components for pool water maintenance that may each be used separately or that may be used together in an integrated system. In some embodiments, the functionality of two or more modules can be merged into one module. While the system is described here in the context of a pool or a spa, other man-made water installations mentioned above may need sanitizer and chemicals to balance the water and can benefit from all or parts of this system. The system and its components can perform their intended function autonomously or extend their capabilities by exchanging information with a database, the user, other pool owners and service personnel through the Internet.

Figure 8:
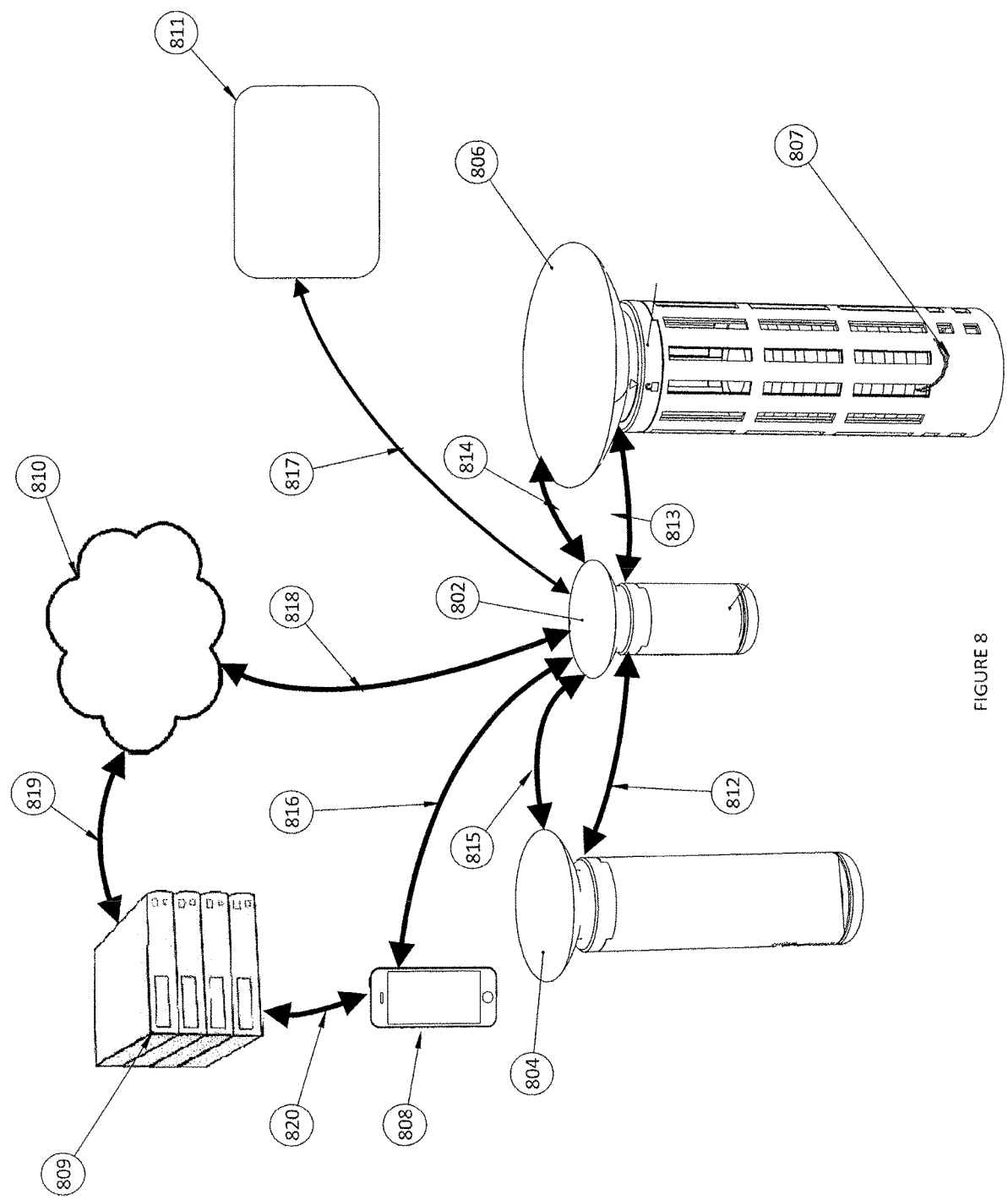
FIG. 8 shows components of a modular pool water maintenance system according to an embodiment of the invention.

FIG. 8 shows one embodiment of a system of this invention including the following: a water quality measurement module 802 containing, e.g., a disposable analyte pad cartridge (not shown), a chlorine dispensing module 806 with its solid chlorine pucks 807, a water balance chemical dispensing module 804 with, e.g., sealed packets of chemicals (now shown) dispensed under water. The system of this embodiment also includes the following modules disposed outside the water: an optional pump control module 811, a user's smart phone 808 that can be used to monitor and control the system and a mechanism that provides communication between the modules, between the modules and the Internet 810 and servers 809 used to store and process data from the system and with the user via the Internet. In a typical use, the measurement module 802 makes daily measurement of the pool chemistry and then commands the chlorine dispensing module 806 to expose trichlor pucks to water when there are no swimmers in the pool. Under control of the optional pump control module 811, the circulation pump is active for a period that is based on the size of the pool, the amount of trichlor needed to bring the free chlorine in the water to a desirable level, the amount of trichlor left in the dispenser and can be exposed to water, the water temperature and other parameters. This process minimizes the amount of trichlor released to the water, enhancing the user experience, reducing cost, and reducing the accumulation of trichlor byproducts that require substantial amount of the pool water to be replaced. The measurement module 802 can similarly instruct the chemical dispensing module 804 to open a number of packets required to bring the water pH into desired level. The sound and current consumption of the circulating pump can alert the user or service personnel to empty the pool baskets or wash the filter. The turbidity of the water can be used to turn on the circulating pump for only the necessary time required to clear the water through the filters and thus save electricity. The components are battery operated and require no installation except for the pump control module that is wired into the pump relay and draws its power from it. This important feature allows the user to deploy a level of pool automation in minutes and save on chemicals, as well as on water use and power.

Figure 1A:
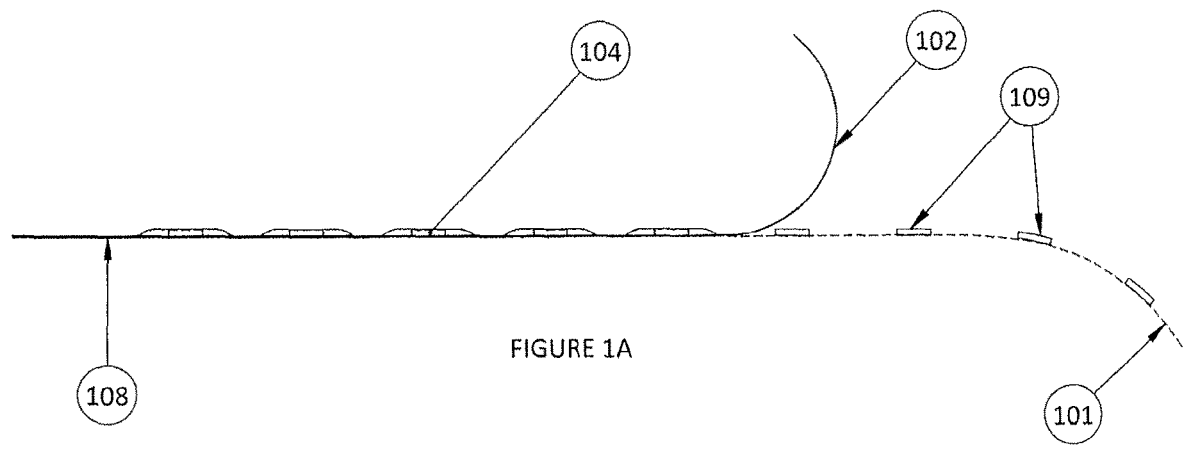
FIGS. 1A-C show three views of a strip of test pads for use in a water quality measurement apparatus according to an aspect of the invention.
Figure 1B:
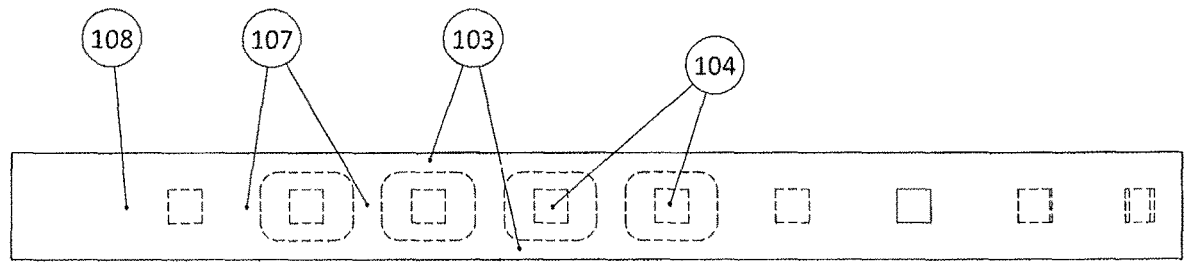
Figure 1C:
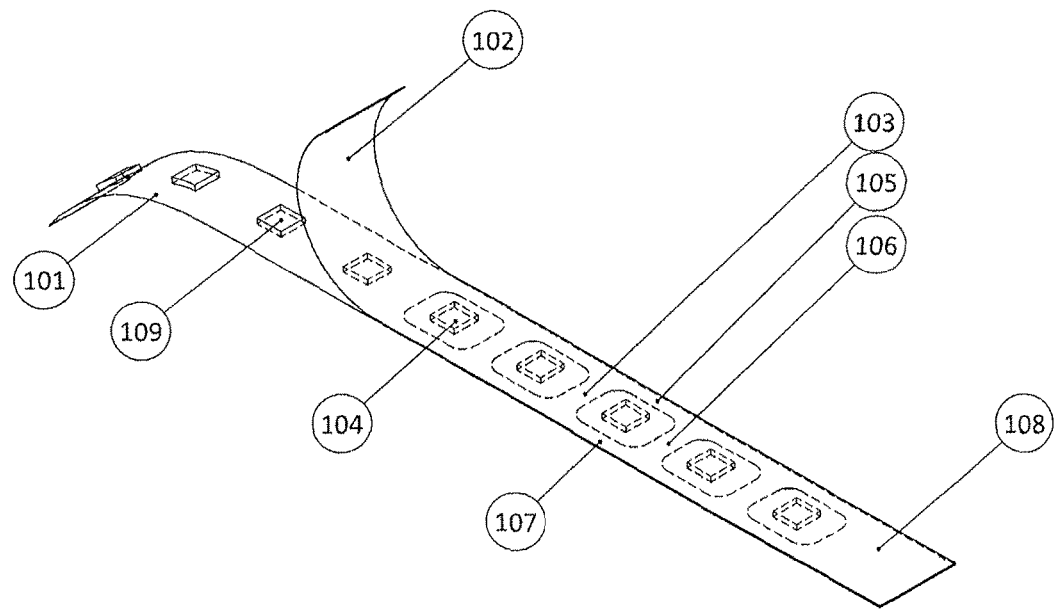
Figure 2:
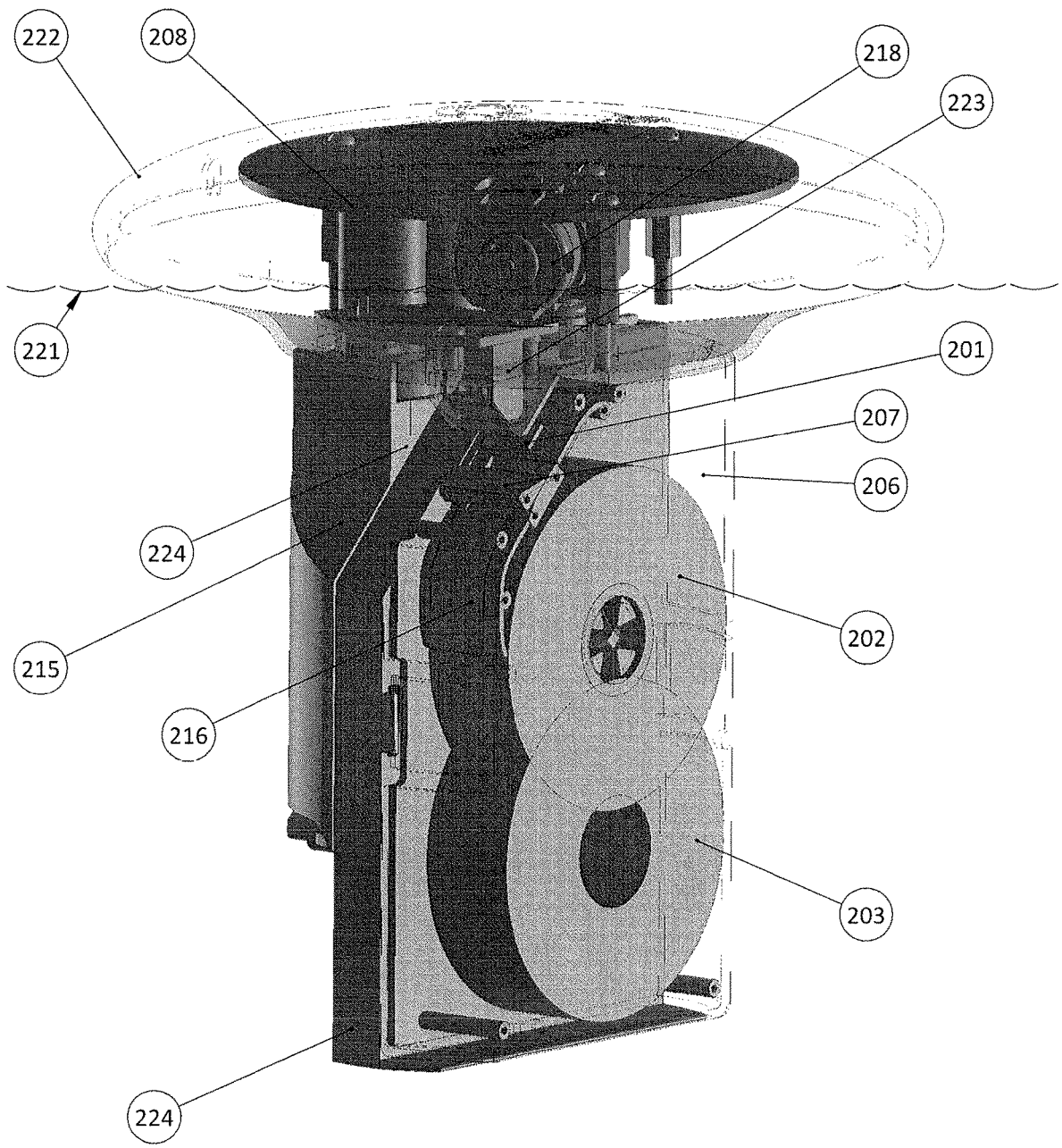
FIG. 2 shows a water quality measurement apparatus according to an aspect of the invention employing the strip of test pads shown in FIG. 1.

FIGS. 1-4 show aspects of the measurement module intended to be floated in a pool. As shown in FIG. 2, an inexpensive disposable cartridge 224 is attached to a buoyancy device 222. The cartridge 224 is submerged in the water 221 and supports a coiled strip 216 of sequential colorimetric pads 201 that can be used to test for, for example, FC using dye N,N-diethyl-p-phenylenediamine and pH using dye phenol red. The strip 216 may also contain a non-reactive pad that remains white in the water and provides periodic optical calibration target (CT). The strip can consist of any suitable pattern of pads, such as a repeated pattern of pH, FC, FC, FC, CT's. The strip 216 is unwound from a bottom spool 203 onto a top pickup spool 202 in a manner that exposes the pads 201 and any other test areas, as described below. A motor 218 controls the movement of the spool 202 and/or spool 203. As explained below, the colorimetric pads are exposed to water and any color change is sensed by an optical reader assembly 208.

FIGS. 1A and B show a strip 108 of test pads 104 outside of a measurement module cartridge 206 shown in FIG. 2 in side view and perspective. In one embodiment, each pad 104 measures roughly 5 mm by 5 mm and is attached to a lower barrier film 101 with contact adhesive and further sealed in a water proof compartment made from circumferential heat seals 103, 105, 106 and 107 formed between lower barrier film 101 and a top barrier film 102. The pad is placed in an offset position inside the sealed compartment so that it can be fully exposed to pool water and the optical reader when that compartment is opened without having to open the next sealed compartment. The term "barrier film" as defined herein is a material that provides an appropriate barrier from liquid water and water vapor to insure the chemical stability of its content over its intended field storage duration. The laminated barrier film can be constructed from specialized suitable transparent film that resists both water and water vapor, allows heat sealing and contains a peel layer. For example, in one embodiment the transparent barrier film construction consists of the following layers from the outside in: (1) A 12-micron biaxially oriented polyester; (2) A vapor deposited aluminum oxide layer as a $H_2O$ barrier; (3) An adhesive 50 micron polyethylene/polybutylene blend as the inside heat seal and peel layer. The waterproof storage compartment is created by a heat seal along the sides 105 and 103 as well as cross seals 106 and 107. Once the top and bottom film are pulled apart under water, the content of the storage compartment is exposed to water. The film is used to carry the exposed pads 109 until the cartridge is fully used and disposed.

Figure 4:
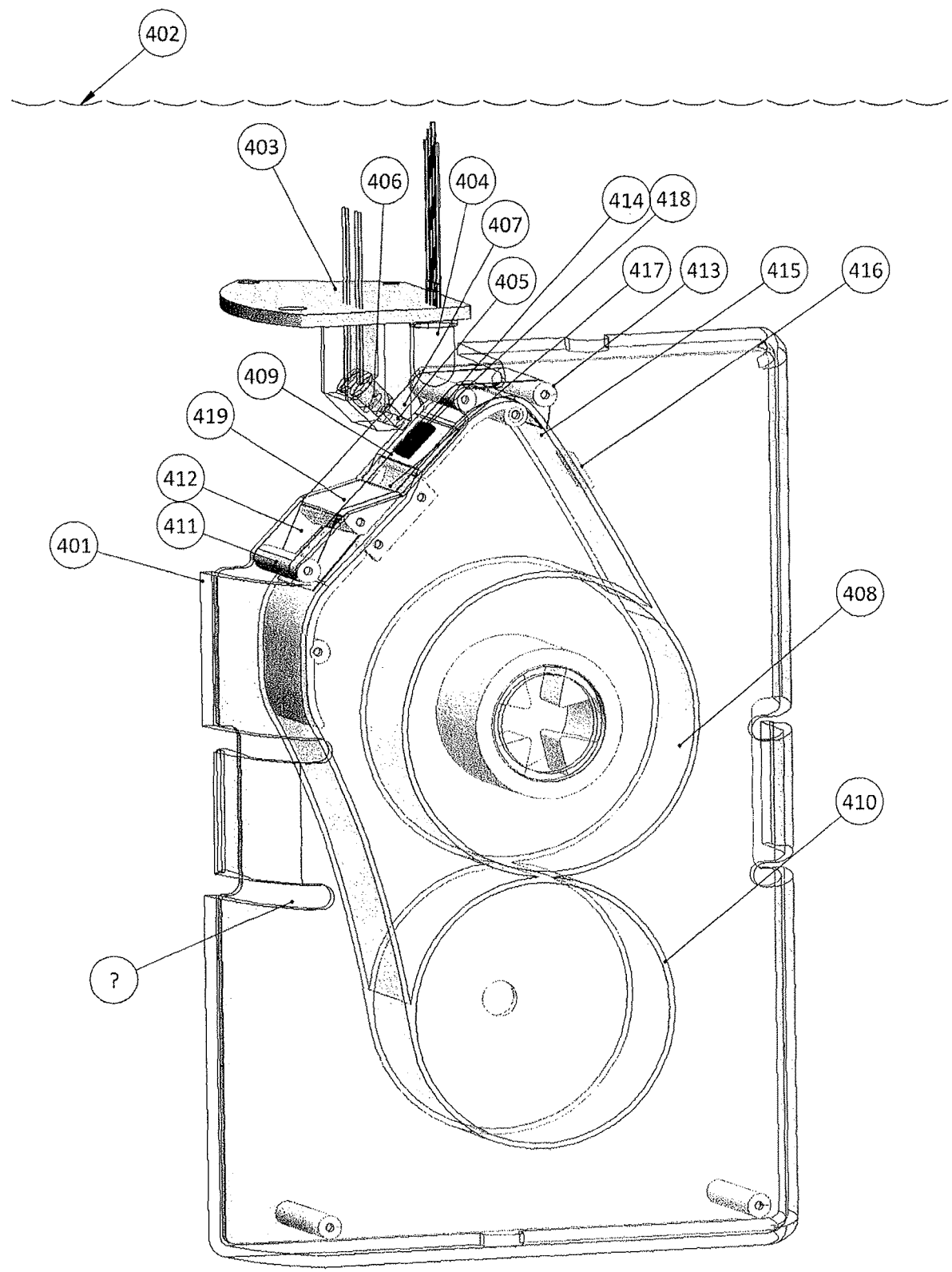
FIG. 4 is a detailed partial view of the water quality measurement apparatus of FIG. 2.

FIG. 4 shows the top of the measurement module cartridge 401 and water sealed optical reader assembly 403 submerged in water 402. As the pickup spool 408 pulls the film strip over platen 409, each sealed pad 410 is moved to position 417 where it is exposed to pool water for a brief period of time and then to position 418 where its color is read by the optical reader assembly 403. To expose the pads 410, the top film 412 is pulled away from the bottom film by moving over wedge 419 and pin 411 while the bottom film 415 carrying the pad is forced by tension created by the pulling to remain on the platen. This action disrupts three heat seals 103, 105 and 107, as shown in FIG. 1, and the pad 410 that was previously completely protected from water by the barrier film is exposed to the pool water. The clear top film is pulled under the optical reader window 407 and, after rolling on pin 413, reunites with the bottom film, trapping the used pads 416 as they are being wound on pickup spool 408. Alternatively, motor driven pinch rollers can pull the film instead of the reel. Pad 414 in position 418 is illuminated by multiple colors sequentially generated by multicolor LED 404. The colors are selected to optimally interact with the color of the pads to provide the best colorimetric data. For FC and pH the colors of red, green, blue were selected. Other LED colors may be selected to optimize the colorimetric response for a particular test pad assay. The light from the LED is formed by aperture 405 to create an illumination circle on the pad and the reflected light is analyzed by a photodiode 406 in optical reader assembly 403. The color information is captured and processed by the on board computer described later. An additional photodiode with a field of view on the side the pad can be used to watch for a dark alignment mark be printed on the strip to help the system stop the motor when a colorimetric pad is centered under the photodiode 406.

Figure 3:
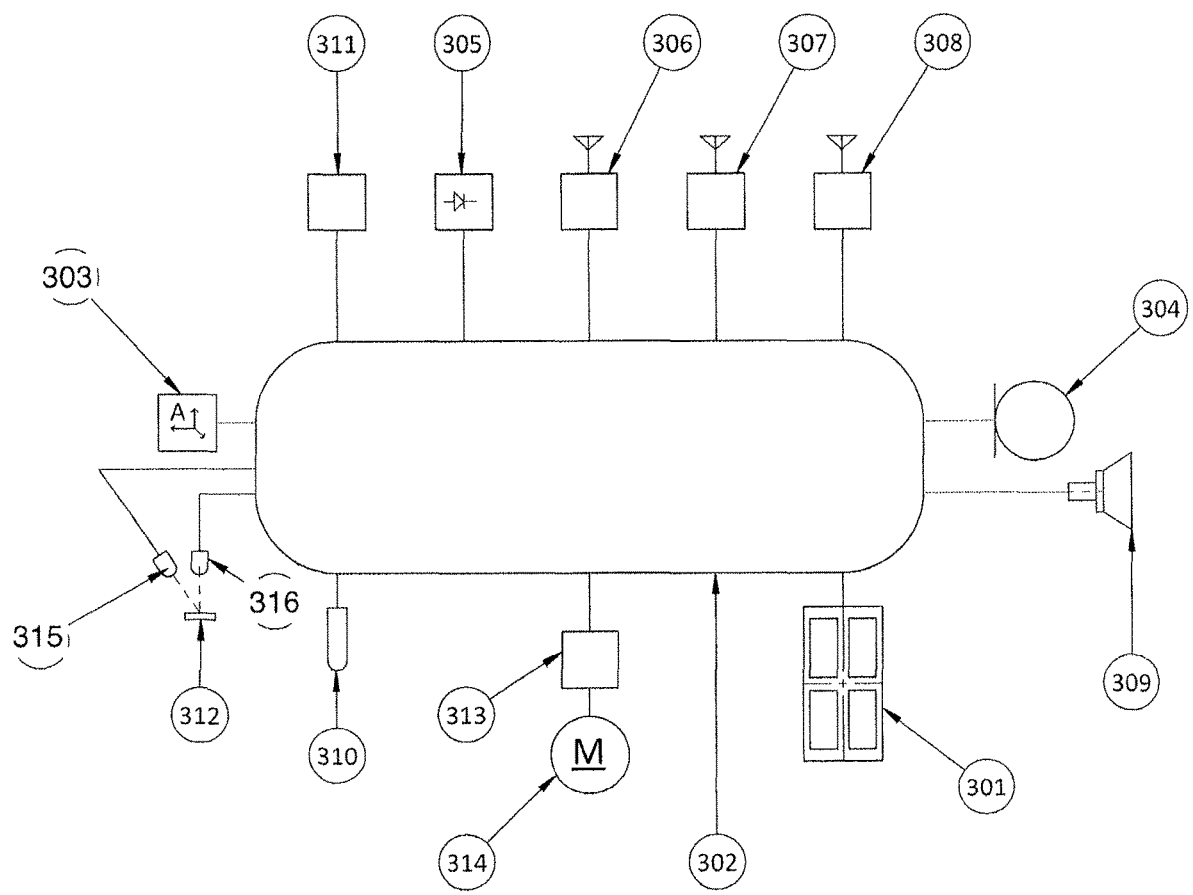
FIG. 3 is a schematic rendering of the sensing and control elements of the water quality measurement apparatus of FIG. 2.

Referring again to FIG. 2, pulling the strip 201 through the platen 207 as described above exposes one pad at a time. The pickup spool 202 in the disposable cartridge 224 is driven from its center by a shaft driven by a gear motor 218 disposed in buoyancy device 222 through a watertight coupling. The motor and motor drive electronics are capable of monitoring current and pulse width modulating the current to control motor speed, such as shown in FIG. 3 as elements 313 and 314, respectively. The optical assembly is also shown as part of the system in 310 and 311 interacting with pad 312 in FIG. 3. Onboard microcontroller 302 controls the operation. This system is battery operated, as shown by battery 215 in FIG. 2 and battery 301 in FIG. 3. The system can be floated in the pool with most of it submerged in the pool water where the buoyant top of the watertight enclosure 222 provides the module its orientation in the water. Without the moisture-proof individual packet, the measurement pad would be quickly degraded by water and humidity and would no longer be suitable for accurate analyte reading. The continuous strip of packets, the non-stretchable water and vapor barrier film that can still be peeled apart when pulled through pins, the method of exposing them one at a time while still submerged in the water or exposed to humidity, the ability to operate this system for an entire pool season on four AA batteries and sell it for less than $100 (compared to commercial water testing systems in commercial pools costing thousands of dollars) and requiring no electrical or plumbing modifications to the pool makes this system an affordable and practical autonomous pool water quality monitoring system that can easily be user deployed.

Continuous daily chlorine monitoring as part of an integrated chlorine dosing system affords the system the ability to calculate chlorine demand. If the demand increases unexpectedly, it often signals an impending algae bloom that can be addressed by adding algaecides before the problem requires more drastic intervention such as complete pool water replacement.

The FC concentration and pH of the pool near the surface of the water are affected by sunlight and outgassing. In order to measure the bulk water rather than this surface water, the module also incorporates a tube with a one-way valve that utilizes the natural bobbing motion of the module in the pool to circulate deep pool water into the measurement module cartridge 224. Alternatively, a fin next to the measurement chamber can circulate nearby water based on gentle bobbing of the module in water.

In FIG. 3, the battery operated measurement module is controlled by microprocessor 302 with associated memory and control circuits. This control and communication system with its attendant sensors can be incorporated into any of the modules described below so that each module's sensors and control functions can be communicated throughout the system. In this example, most of the sensors are built into the measurement module that serves as a communication hub to command other modules' operations or advise the user of certain actions that should be performed.

The measurement module may further incorporate a 3-axis accelerometer 303 to measure water movement indicative of swimmers. Accelerometer 303 generates and communicates an orientation to microprocessor 302. It may further incorporate a hydrophone 304 (described below) that captures splashing sounds of swimmers. The presence of swimmers can be used to stop chemical dispensing into the pool, or alert the pool owner of potentially unsafe use of the pool by underage swimmers.

The measurement module may further incorporate a light sensor 305 to measure sunlight exposure. Light sensor 305 generates a sensed light signal and sends it to microprocessor 302. Sunlight degrades chlorine in the pool and this information can be used to determine when to dose and how much chlorine is needed based on current or historical sunlight exposure.

The measurement module may further incorporate a temperature probe 310 for generating a water temperature signal and sending the signal to microprocessor 302. The water temperature information may be used, e.g., to determine the rate of chemical reactions and outgassing that consume chlorine in the water, which is temperature dependent. The length or extent of exposure of solid chlorine to the water is adjusted automatically or by the user based on this information.

In addition to the water temperature probe 310, the measurement module may further incorporate an air temperature probe 311 that generates and sends an air temperature signal to microprocessor 302. The information from these sensors, when combined with wind and relative humidity data obtained from an Internet weather service, allows the device to calculate the evaporation rate in order to estimate the refill rate that increases the total alkalinity and calcium hardness from fill water so that remedial action may be taken.

Figure 15:
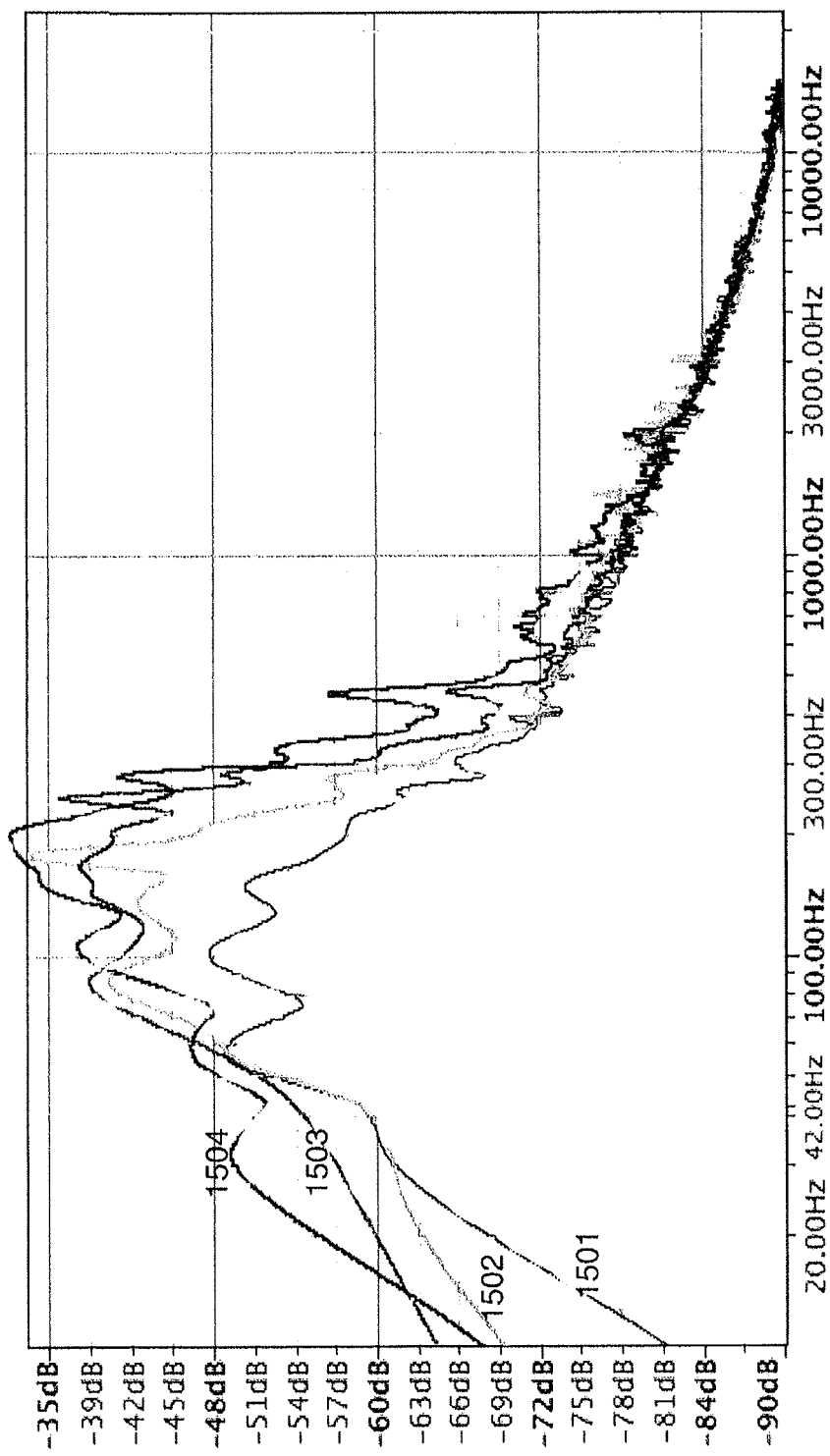
FIG. 15 shows a spectrum of hydrophone-derived signal from the pool under various conditions.

The hydrophone (or water coupled microphone) 304 can pick up sounds in the water, and the microprocessor 302 can extract features from these signals. FIG. 15 illustrates the frequency spectrum derived by FFT process for the hydrophone-derived signal 1504 where distinct swimmer activity can be seen in the 800-1000 Hz region when compared to spectrum 1501 showing similar spectrum with no swimmers in the pool. Spectrums 1502 and 1503 illustrate the frequency spectrum derived by FFT process for the hydrophone-derived signal where the circulation pump is active at slower and faster speed, respectively, can be seen in the 100-300 Hz region when compared to showing similar spectrum 1501 with the pump is not active. The system can learn the exact sound of each pool by monitoring the sound and comparing it for any acoustic condition. In addition to the frequency fingerprint, the system can apply machine learning algorithms such as Hidden Markov Models to determine whether someone jumped into the pool or is swimming in the pool so that the system can avoid dosing the water with chemicals or releasing gas. Sound signals from the hydrophone 304 can also be used by the microprocessor 302 to determine whether the filter pump is on so that the system can dispense chemicals or make measurements after a suitable delay to insure well circulated water to disperse the chemicals. Sound signals from the hydrophone 304 can also be used by the microprocessor 302 to infer the filter pump speed and load from which the state of the filtration system can be deduced so that the system can alert the user or service person to clean the filters, empty the baskets, and/or address unusual bearing sounds from the pump that signal imminent pump malfunction. The microphone 304 can also identify rainfall that indicates water dilution requiring chemical dosing adjustment, the sound of a cover being pulled over the pool that reduces chemical need but may trap floating modules under the cover, and any other activity that generates acoustic energy in the pool.

The measurement module may further incorporate an acoustic based or ultrasound based transducer 309 in addition to the hydrophone 304 that communicates with other similarly equipped nearby modules to control them or receive their status. These communication links are illustrated in FIG. 8 as elements 812 and 813.

The measurement module may further incorporate RF transmitters such as Bluetooth 306 (aka BLE), cellular modem, 307 or Wi-Fi 308 with their respective antennas. These RF communication devices are used to communicate between similarly equipped modules (see elements 814, 815 and 817 in FIG. 8), to the Internet via Wi-Fi or cellular modem (See element 818 in FIG. 8) or BLE via a BLE-to-WiFi bridge or to the user's smartphone via BLE or Wi-Fi (see element 816 in FIG. 8).

The system can be coupled via RF link to the Internet from which it can receive further environmental information from a weather service database (pollen count, sun coverage including UV index, rain fall, conditions leading to algae bloom, temperature, wind, relative humidity, etc.). Such local weather conditions can be used to provide data to estimate chlorine demand and the impact to water clarity from blown-in debris.

Information from multiple systems in pools in the same locale can be analyzed together to further increase the reliability of any one system since pools in the same area are exposed to the same environmental conditions. This collaborative network of system sensors provides each sensor the context necessary to interpret its measurement data and measurement frequency strategy to further optimize the water treatment as described below.

These sensors and others described below, the microcontroller, batteries, motor, motor drive and communication modules can also be incorporated in a similar manner to other modules in the system described below.

Puck Based Chlorine Dispensing Module

FIGS. 7A and 7B show two configurations of a floating chlorine dispensing module (718 and 719, respectively) that may be used alone or as part of a system of other modules, as described above. The chlorine dispensing module has a buoyant top 709 that enables the module to float in the pool water 717. The chlorine dispensing module has a battery 701 and contains suitable disinfectant such as trichlor, or bromine pucks, granules or powder 702. For example, the trichlor pucks based system controls the appropriate amount of FC dissolving in the pool water, either from a user command or in response to information from a water quality measurement module as described above. The automatic dispensing floating module contains a motor 704 operated mechanical shutter made up of a two nested slotted 715 and 714 cylinders that can rotate with respect to each other. As shown in the configuration of FIG. 7A, the motor 704 of module 718 has rotated the outside cylinder so the content of the inner cylinder is exposed to pool water through slots 702. As shown in the configuration in FIG. 7B, the motor 704 of module 719 has rotated the outside cylinder so that the outside cylinder's slots now occlude the inner cylinder slots and the module's contents are shielded from the pool water. In this manner, the module's electronics control module 710 can control the amount of FC delivered to the pool water from the trichlor pucks in the module.

Current floating dispensers are the most popular form of dosing pools. They have slits that are manually set by the user to adjust their opening and hence control the amount of sanitizer dissolved from the unit into the pool water. However, many factors affect the chlorine demand in a pool: amount of sunlight which breaks down chlorine, swimmer load, pollen and leaves blown into the pool, rain water, algae growth if insufficient chlorine levels are maintained, and skin cells, suntan lotion, and other debris caught in the filter. To complicate matters, the rate of chlorine dissolving from these dispensers or from an inline chlorinator is also affected by the surface area of the slits exposing pucks to water, the number of pucks in the floating dispenser, their surface area that changes as they dissolve, water temperature, circulating pump activity which tends to increase the dissolving rate to mention but a few. Clearly users are not able to manually adjust the setting on the floating dispenser to accommodate all these factors which results in either under dosing with its associated health risk and possible algae bloom or over exposure which results in burning eyes, bleached hair and swim wear, extra cost of chemicals and faster build-up of CYA, a residual part of the trichlor molecule, which reduces the effectiveness of chlorination and eventually requires water dilution to reduce its concentration, often in excess of thousands of gallons in a typical in ground pool.

The present invention incorporates all of these measured variables as well as a daily measurement of chlorine level to dissolve the precise amount of chlorine in the pool on an hourly basis. It measures directly or receives via intra-module communication described above variables such as water temperature, current FC levels, time of day, exposure to sunlight, pool usage, presence and activity of other oxidizing equipment such as salt water chlorine generators or ozonators, circulating pump activity, historic FC consumption, pool size, weather, rainfall, and computes the amount of time to open the shutter on the FC dispensing unit when people are not using the pool to reduce their encounter with undiluted chemicals and thus creates an ideal swimming experience.

Unlike existing floating dispensers that must be loaded with pucks of trichlor requiring the user to touch the highly oxidizing and odorous puck, this unit utilizes a cartridge that consists of solid or granular trichlor wrapped in a water dissolvable film in order to allow the user safe and pleasant handling of this chemical and avoiding the over 400 consumer injuries each year from such pool chemicals as reported by the EPA. The water dissolvable film 716 (shown in FIG. 7C) wraps the sanitizer pucks 702 and fits into the dispensing unit 708. The water dissolving film can be made of polyvinyl alcohol (aka PVOH or PVA).

Concentrated trichlor in this type of popular floating dispenser often generates by-products including nitrogen trichloride that has a pungent odor that most people associate with the unpleasant smell of chemicals in and around pools. The present invention traps this gas generated by trichlor in the reservoir in a sealed compartment 709 at the top of the dispenser and utilizes a solenoid or motor activated valve 711 to vent it through opening 712 when the pool is not in use such as nighttime in order to minimize this very unpleasant odor while the pool is in use. The floating dispensing module gathers pool use information from one or more of the sensors described above to ascertain if swimmers are in or near the pool. These sensors were described above in the water quality module that can communicate this information to this module or the same sensors can be built into this unit.

A magnet 707 is placed on top of the cartridge and a magnetometer in the on board electronics 710 measures the magnetic field that changes as the trichlor is dissolved and the magnet moves further from its home position. This allows the chlorine dispenser to alert the user to install a new cartridge before the unit runs out of chlorine. Alternatively, the hydrophone and ultrasonic transducer described above can be used to reflect sound from the top of the trichlor stack and calculate the height of the stack by measuring the time for the echo to arrive at the hydrophone.

Figure 11:
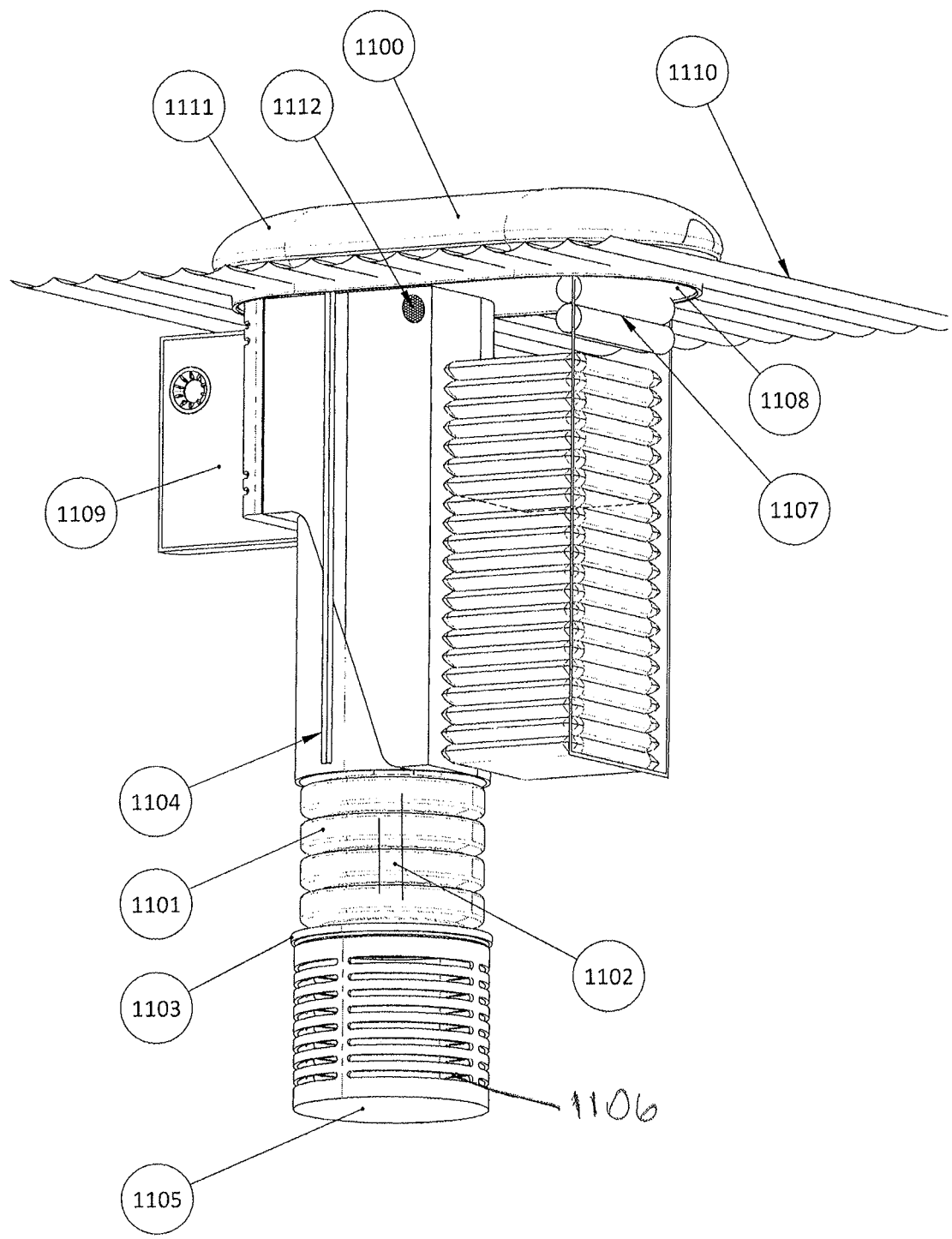
FIG. 11 shows an integrated floating pool water maintenance apparatus according to an aspect of the invention.

Trichlor pucks in contact with pool water will dissolve at varying rates depending on the water flow and other parameters noted above and thus the flux of chlorine cannot be completely stopped. In another embodiment shown in FIG. 11, a complete system 1100, floats with water line 1110, where the motors and electronics are housed in the unit's cap 1111. System 1100 dispenses trichlor from a stack of slow dissolving pucks 1101 which can be completely removed from contact with pool water by lifting them into a bell jar like reservoir 1104. The pucks 1101 have a hole in the middle through which worm screw 1102 (shown in phantom) passes. The worm screw engages a lift plate 1103 to lift the stack of chlorine pucks into the reservoir 1104 and lower them to the dispensing area 1105 where they are exposed to the water through slits 1106. The worm screw is driven by a motor connected to a microprocessor capable of measuring the current in the motor and hence the limits of travel of the lift plate which stalls when fully lowered or raised. The number of turns between the position of fully lowered lift plate to its fully raised position provides a measure for how much of the pucks on the stack have yet to be dissolved in the pool water and when the user must be alerted to refill the device.

The gas in the reservoir is produced by the dissolving trichlor pucks or can be pumped in. When the pucks are raised above the water into the reservoir's gas layer, the chlorine dispensing into the water ceases completely. The gas layer height can be controlled by the on board microprocessor and kept right below the lift plate in its up most position by using a water level capacitive sensor as described in US 2013/0313204. In order to control the device's buoyancy and maintain the gas at the right level as measured by the capacitive sensor described above, a pump (not shown) or a motor actuated valve 1112 can be opened to vent the gas when no one is near the device. It can be appreciated that any of these modules can be integrated into one unit or deployed independently.

This embodiment also includes chemicals in packages on a folded strip 1120. To dispense these chemicals, the strip is pulled by pinch rollers 1107 past ceramic blade 1108 to disrupt the packages and dispense the chemicals they contain.

Submerged Powdered or Gel Chemical Dispensing Module

Figure 5:
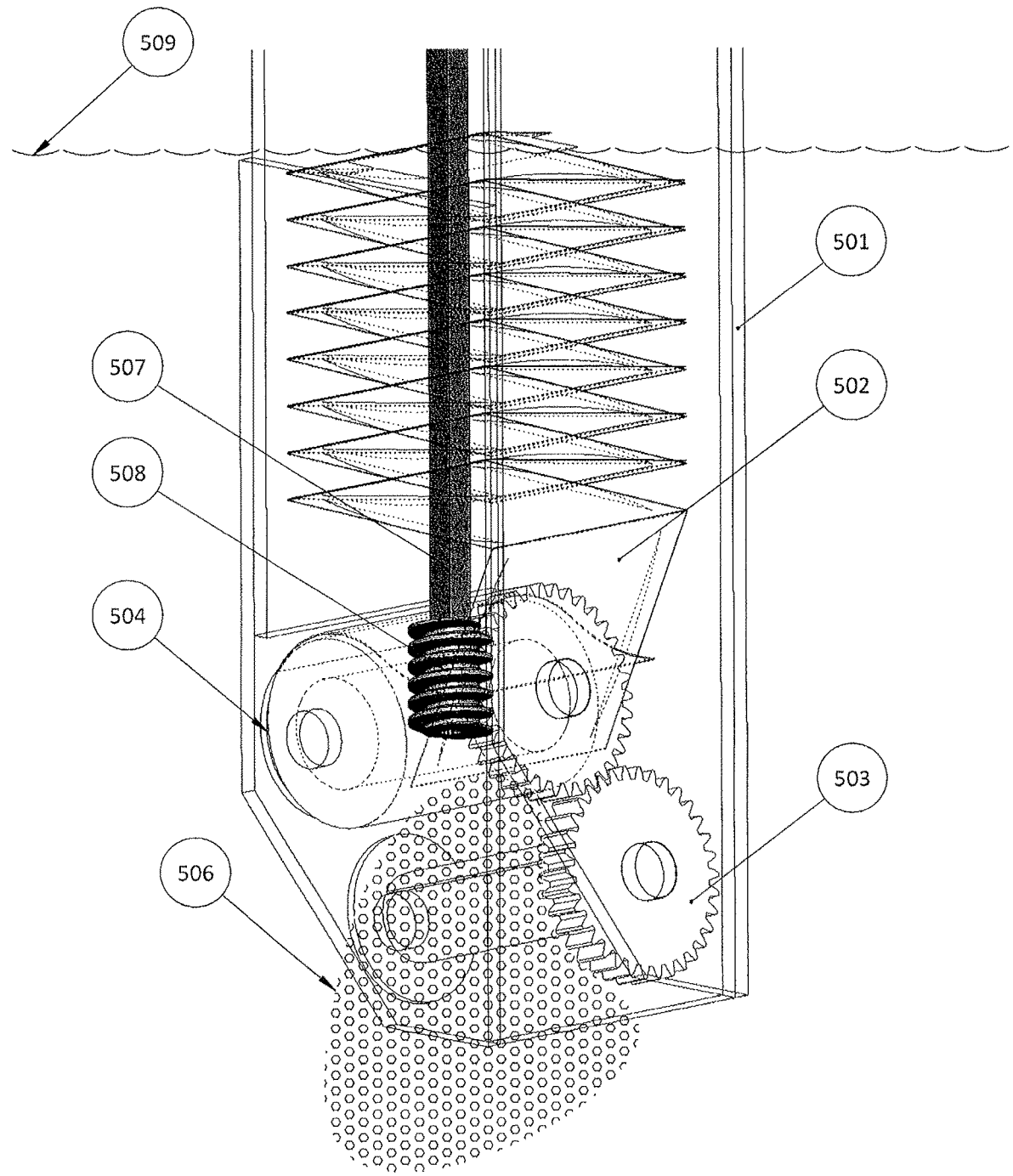
FIG. 5 shows a chemical dispensing apparatus according to an aspect of the invention.

Other chemicals may need to be dispensed into the water installation. FIG. 8 shows a floating water balance chemical dispenser module 804 with a buoyant top utilizing cartridges, e.g., a disposable cartridge shown in FIG. 5. FIG. 5 shows the cartridge 501 containing a strip 502 of packets of chemicals enclosed in a barrier film. This film does not react with its contents and minimizes moisture entering the packet and reacting with the chemicals stored within it (and thus degrading their performance or activating them, causing gas release or package failure). Each chemical has its water exposure limit over its intended in-field and shelf-life use case. The chemicals can be in solid, granular, powder, gel or liquid form. For example, most chlorine-based sanitizers outgas and begin to decompose when exposed to any moisture. The outgassing of the chemicals compromises the packet seal, which in turn lets more water in and activates the chlorine that can completely destroy the film. Therefore, in one embodiment this film is specially constructed as a multilayer laminate and filled and sealed with special equipment that does not compromise the film's barrier properties. For example, the laminated chemical barrier film can be constructed from the following layers from the outside in: (1) An outer layer protecting the aluminum foil such as 12 micron biaxially oriented polyester; (2) An adhesive; (3) A moisture barrier such as 0.009 micron aluminum foil; (4) An adhesive; (5) A 50 micron polyethylene/polybutylene blend to provide the peelable heat seal and protect the aluminum from the inside of the packet.

The top and bottom film are peeled apart by winding them on two geared bobbins 503 and 504 under the control of the embedded controller's gear motor (in the buoyant compartment above the cartridge 501, not shown in FIG. 5) coupled to the gear via rotating shaft 507 and worm gear 508. When the shaft rotates the worm gear, the bobbins rotate in opposite directions pulling the top film and the bottom film apart and separating their heat seal. Separation of the film pieces exposes the chemicals in the packet and allows them to dissolve in the water, as shown schematically by arrow 506. Alternatively, slitting blades can disrupt the moisture impermeable packets and disperse their content into the water. The cross seal between packets (similar to that shown as element 107 in FIG. 1) requires more force than the side seals. The increased force can be used by the on board processor which monitors the motor current to signal that a full packet has been peeled.

In yet another embodiment, the packets are driven by two textured pinch rollers (such as the pinch rollers 1107 shown in FIG. 11) along the sealed edges of the strip of packets while blades (such as, e.g., the ceramic blades 1108 shown in FIG. 11) slice the top of the packet as it moves along so that its content can be dispensed into the pool water in response to an integrated measurement unit (such as unit 1109 in FIG. 11) as described above. Alternatively, a wheel with sharp spokes is spring loaded into the packets and pokes holes in the film to allow water to mix with the enclosed chemicals and disperse them in the pool.

The chemicals in the packets might consist of trichlor, dichlor, calcium hypochlorite, lithium hypochlorite, sodium hydroxide (lye) to drive the pH up to balance the trichlor pH down effect, algaecides or phosphate removers to prevent algae growth, sodium bicarbonate (baking soda) to raise the total alkalinity (TA), or sodium bisulfate or hydrochloric or sulfuric acids to lower the pH when using hypochlorite chlorine, or potassium monopersulfate (MPS) non-chlorine shock. Each of these chemicals is packaged in its own cartridge that is sensed by the chemical dispensing module via on board optical detectors detecting an optical pattern at the top of the cartridge.

Figure 12:
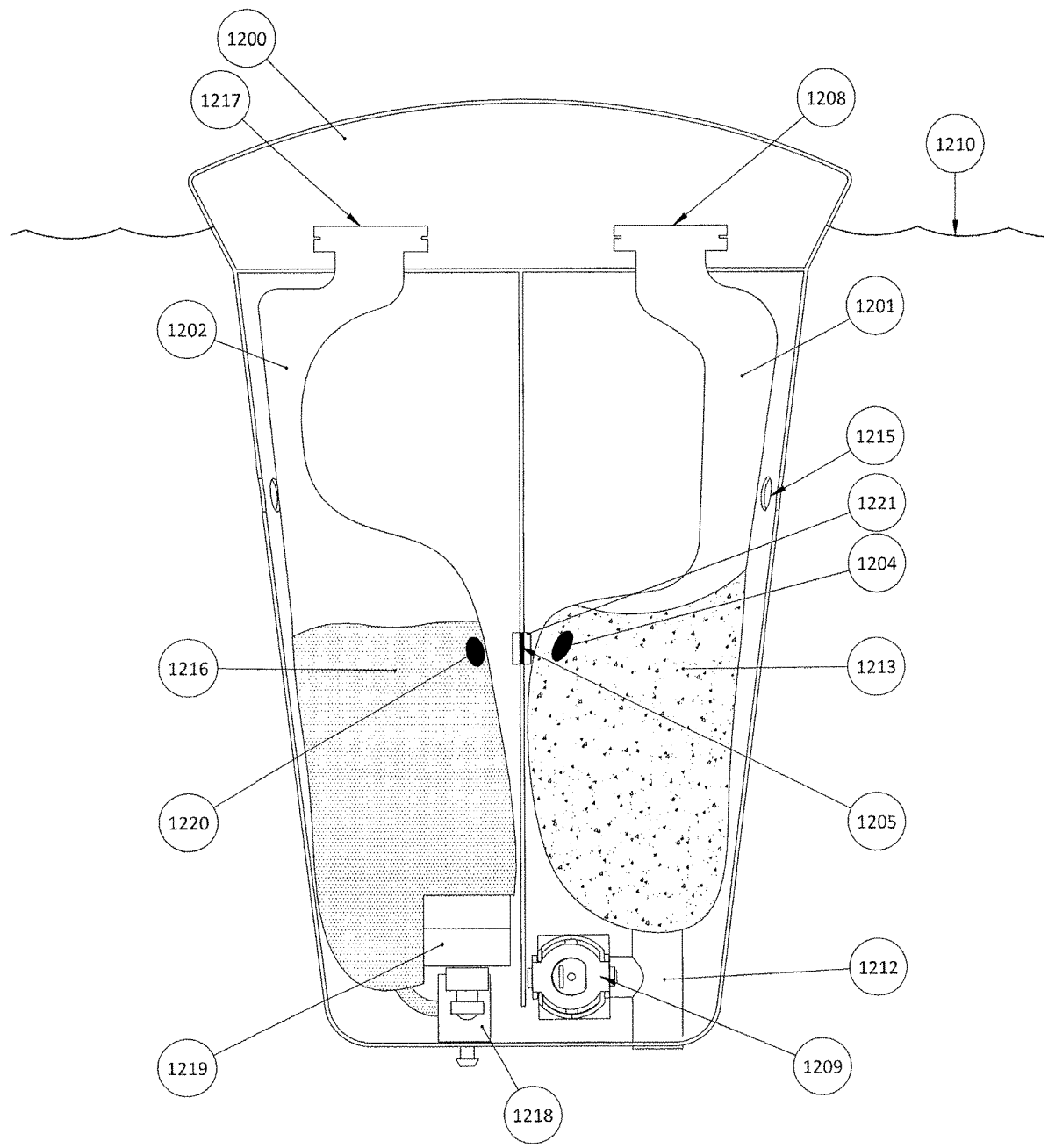
FIG. 12 shows an integrated floating pool water maintenance apparatus according to an aspect of the invention.

In yet another embodiment of the floating integrated dispensing unit 1200 as shown in FIG. 12, the powder chemicals are stored in a collapsible bladder 1201 made of suitable water impermeable film. Dispensing chemicals whose density is close to water from a submerged rigid dispenser of a floating unit changes the buoyancy of the unit and can cause it to tip over. In this embodiment, the chemicals are stored in bladder 1201. The bladder changes its volume as material is dispensed and pool water enters the device through holes 1215 and thus keeps the device's buoyancy nearly constant and floating at the same level over the water 1210. The powder is dispensed into the water using a dispenser 1212 driven by motor 1209 in a waterproof compartment with electronics and battery power source. The dispenser prevents water from entering the bladder and is described further in FIG. 14 below. The user can fill the bladder through filler cap 1208. A suitable magnet 1204 attached to the bladder wall and magnetic field detector 1205 are used by the on board microprocessor to calculate the remaining material in the bladder. The chemical dispenser can thus automatically dose the pool when it receives a command from the water quality measurement module using the communication mechanism described above.

The chemical dispenser can monitor the cartridge becoming empty by sensing the motor current drop due to lower torque with no film to peel and reporting back to the user to replace the cartridge.

For example, calcium hypochlorite packets and sodium bisulfate packets in two different cartridges can be controlled independently depending on what is needed, or in a fixed ratio in the same cartridge.

As an additional example, lithium hypochlorite and baking soda cartridges can be used in different cartridges.

As an additional example, dichlor and baking soda can be delivered from two different cartridges.

As an additional example, potassium monopersulfate (MPS) non-chlorine shock and lye can be delivered from two different cartridges. This combination could be used in the non-halogen Nature$^2$ system that uses silver and zinc ions in conjunction with MPS as an EPA-approved disinfectant.

As an additional example, fragrance or other chemicals can be delivered from a cartridge.

Multiple cartridges of one chemical such as trichlor can be deployed so that when one is empty the full one is deployed and the user has a period of time before having to replace the empty cartridge.

Submerged Liquid Chemical Dispensing Module

FIG. 12 also shows a liquid dispenser for reagents such as muriatic acid 1216 to adjust for calcium hypochlorite powder. The liquid reagent is stored in a bladder 1202 adjacent to bladder 1201. It is filled through cap 1217. It has a similar magnet 1220 and sensor 1221 to detect remaining reagent in the bag. It is dispensed through bellows pump 1218 driven by motor 1219 in a housed in watertight compartment with its electronics and power source.

Non-submerged Chemical Dispensing Module

Figure 13:
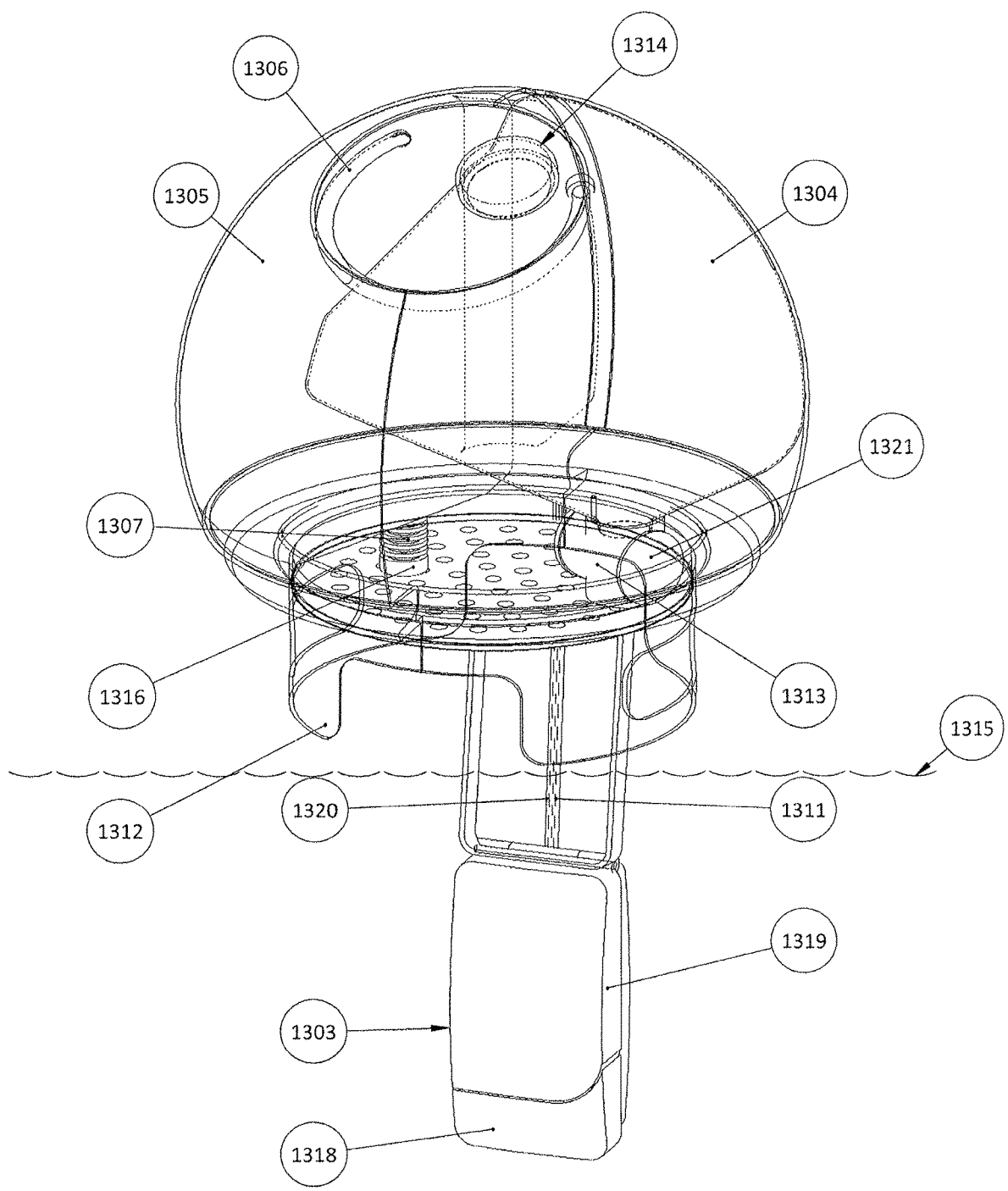
FIG. 13 shows an integrated pool water maintenance apparatus above a pools skimmer port according to an aspect of the invention.

In some situations it is desired to dispense the chemicals from a non-floating module. It should be noted that the mechanisms described above can be used in this configuration where the unit 1301 as described in FIG. 13 sits on top of a skimmer port held with flange 1312 or on the pool's edge with its dispensing ports right over the water 1315 or floating on a buoyant platform above the water. The measurement unit 1303 is as was described above and is incorporated into this unit where at least the measurement area (i.e., where the pads are opened) is submerged in water. Water-sealed compartment 1318 contains the electronics to monitor the pad, the microphone, temperature sensor, water flow sensor, water level sensor, and the pad drive motor. Cassette 1319 contains the sealed and used pad and film as described above. Cable 1320 connects the electronics in 1318 to the main electronics control box, and two of its leads serve as capacitance water height detector 1311 as described in US 2013/0313204. The water level measurement allows the unit to automatically stop dispensing chemicals if it is out of the water or while deployed on the skimmer to report back to the user if pool water level is too high or too low. The temperature is used to determine the chemical dissolution rate and report to the user. The water flow detector is used to insure that chemicals are added only with the pool's circulating pump is active and thus insure that the chemicals dispensed are rapidly dispersed in the pool water. The microphone is used as both pump and swimmer detector to insure that chemicals are only added when no one is in the pool as a measure of safety. The measurement unit pads are protected from water and humidity with the water impermeable film, and are exposed to pool water one at a time as described above.

The calcium hypochlorite reservoir 1304 is filled via port 1314, and it has a dispensing port 1313 with dispensing mechanism 1321 described further below. The reservoir has an angled bottom to insure that all the powder flows to the dispenser via gravity.

Figure 14A:
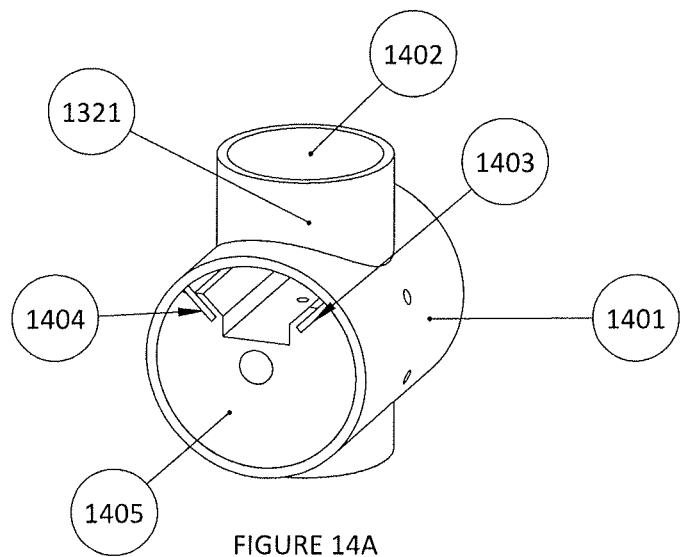
FIGS. 14A-C show a powder-dispensing valve in three different positions according to an aspect of the invention.
Figure 14B:
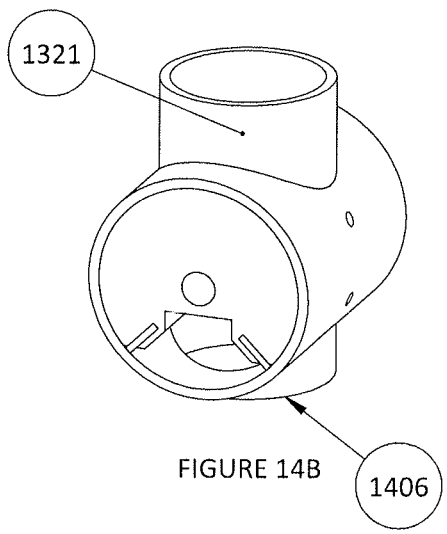
Figure 14C:
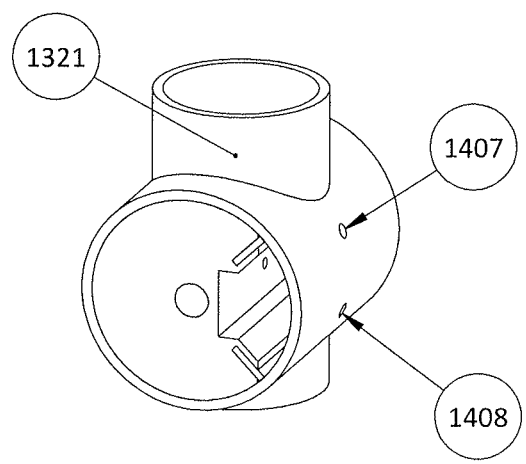

The powder dispenser 1321 is shown in 3 positions in FIGS. 14A-C. In the load position shown in FIG. 14A, the sealed chamber is loaded with a fixed known volume of powder from a reservoir via port 1402. It is sealed from water via wiper blades 1403 and 1404. It is rotated in a drum 1405 via an electric motor. In the dispense position shown in FIG. 14B, the drum 1404 is rotated 180 degrees, and the powder is dropped into the water via port 1406. If this dispenser is operated under water, it is imperative that water will not mix with the dry powder. Therefore, in the water empty position shown in FIG. 14C, air from a small on board pump is routed through port forcing the water that may have entered the dispensing chamber while it was open to dispensing port 1406, through water evacuation hole 1408. The dispenser having been emptied from water can be now be rotated to the load position of FIG. 14A to complete the dispense cycle.

Adjacent muriatic acid reservoir 1305 with its filler port 1306 utilizes a bellows pump 1307 at is base to dispense a measured amount of acid into the water via port 1316.

In addition the module can incorporate a camera and light 1317 to take a picture or sense reflectivity and color of the skimmer basket and alert the user or service personnel when it is full of debris and requires service.

The module may incorporate other sensors, communication and processing means as described above.

In addition to the example described above, this unit or the submerged units can be used in saltwater pools where chlorine is generated by electrolysis. The unit can measure and balance chlorine by adding its own chlorine when peak demands require it, turn off the generator via RF signal to a remote relay unit when too much chlorine is generated and add acid to balance the pH of the pool water.

Turbidity

Figure 9:
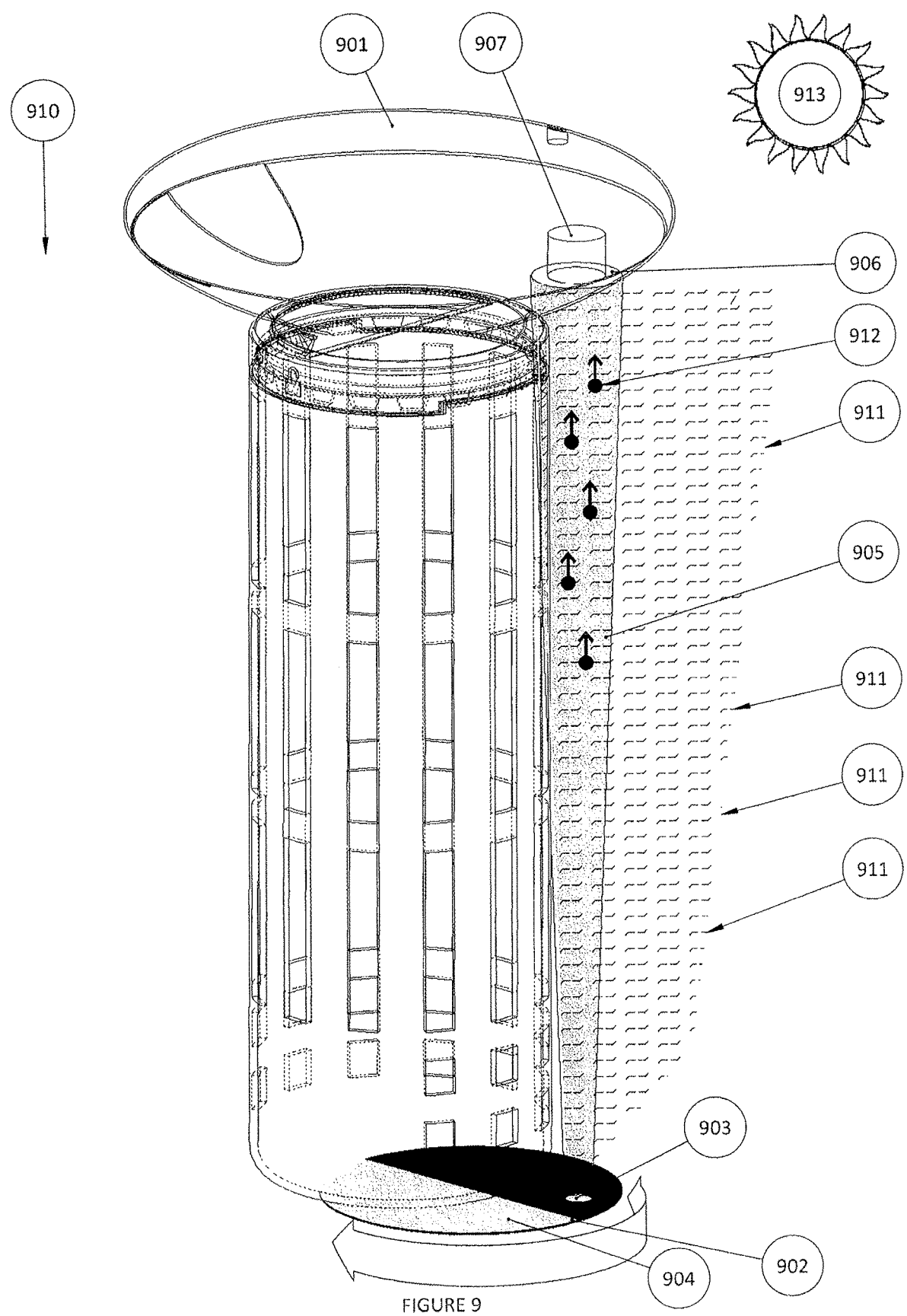
FIG. 9 shows a water turbidity monitoring apparatus according to an aspect of the invention.

As shown in FIG. 9, the floating module 901 may further incorporate an optical turbidity measurement of pool water using a photodiode 907 with a pinhole, aimed through lens 906 through the water at target 902. This ultra-low power turbidity measurement utilizes sunlight 913 to illuminate the target through the pool water. Small particles primarily in the 10-1000 micron range in the pool water scatter sunlight 912 reflected from the target toward the collecting lens 906. That scattered light reduces the contrast between the black and white portions of the target in an amount proportional to the concentration of particles in the water. An eccentric cam moves the spring mounted photodiode 907 laterally a small distance causing it shift its focus between the white 903 and black 904 portions of target 902. The white portion serves as a reference measuring the intensity of the sunlight and the black portion allows the photodiode to see the scattered light. The ratio between these two measurements is proportional to the scattered light in the pool water and is further used to control the filtration cycle of the pool. By turning on the pump only when there are particles to be filtered and stopping the filtration when they have been removed from the water, considerable power can be saved.

Pump Control Module

Figure 6:
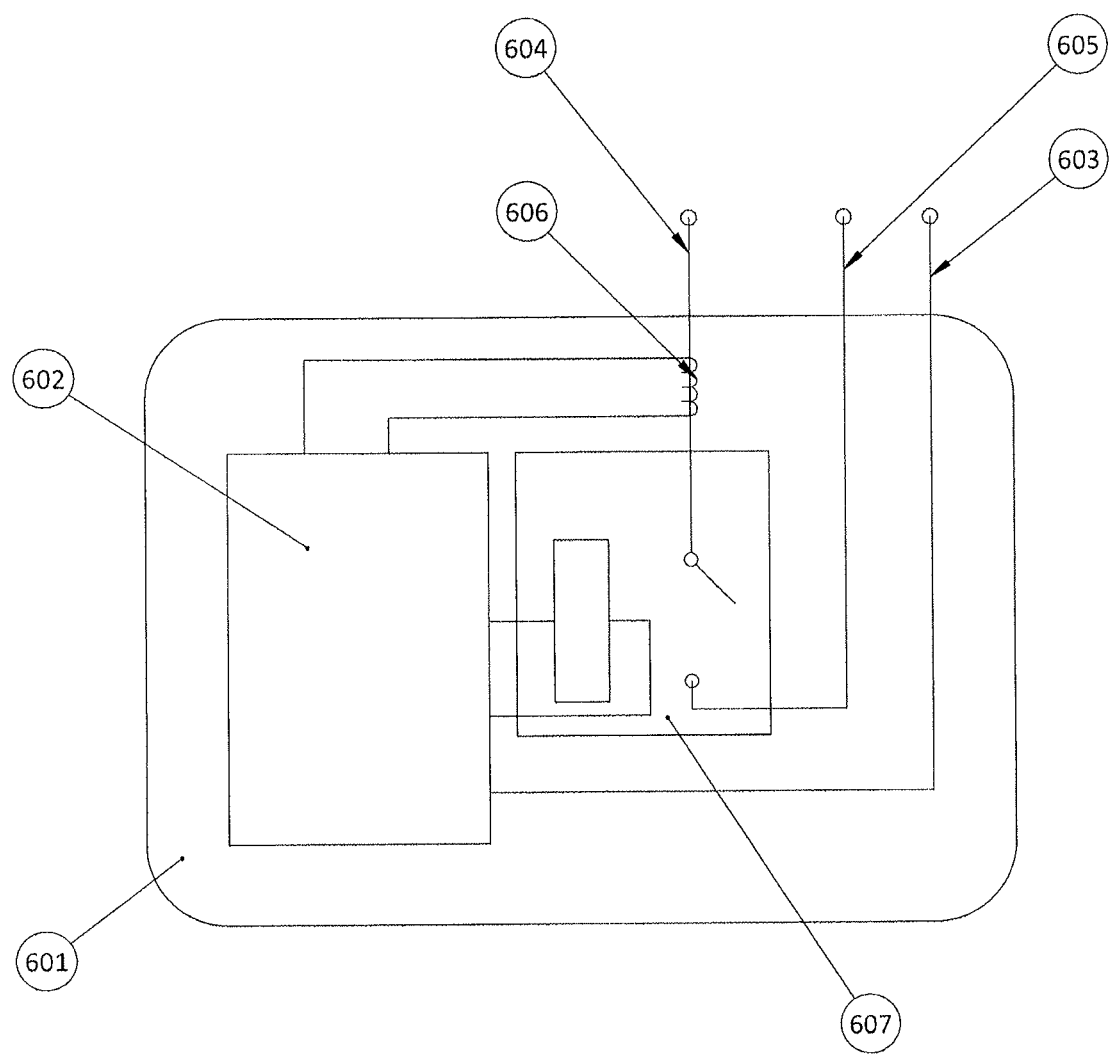
FIG. 6 shows a water pump control apparatus according to an aspect of the invention.

FIG. 6 shows a pump control module that may be used alone or in conjunction with the other modules described above. In one embodiment, an electronic module 601 switches on the filter pump when receiving an RF signal from the water quality measurement module to, e.g., keep the water turbidity below a target level. The unit's relay 607 can be wired in parallel with the pump control relay 604 and 605 without running additional wiring to the pump. The activation of the pump controller based on turbidity instead of hard wired timed operation of the pump allows for optimal use and significant savings of electrical power.

The pump controller senses the voltage via terminals 603 and 604 and current via monitor coil 606 around the pump activation wire by the pump and compares it to previous records. Increase in current over a few days suggests that the skimmer and pump baskets might be clogged with leaves. Increase in current over a longer period of time indicates when the filters develop backpressure and require cleaning. This information is communicated to the user or to a service provider via the RF communication link such as shown as element 817, 818 and 809 in FIG. 8, which makes it available on a web page hosted on the servers, or via elements 817 and 816 directly to a nearby smart phone.

Figure 10:
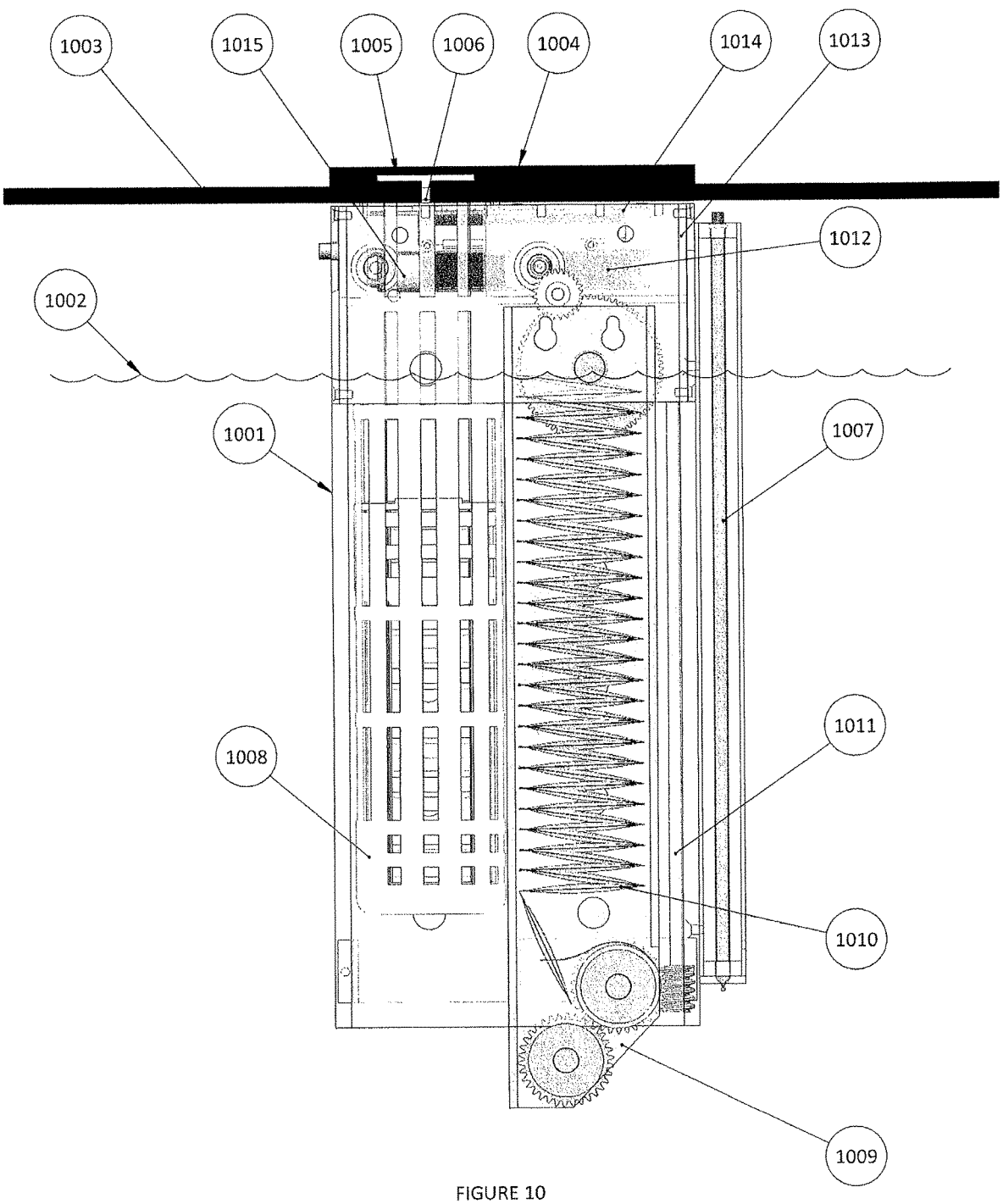
FIG. 10 shows a spa water maintenance apparatus according to an aspect of the invention.

FIG. 10 shows a typical spa configuration of the system where several modules and an alternative sensor can be combined for a particular system configuration. In this configuration a single enclosure 1001 is suspended via strip hanger 1004 off the ledge of a typical spa 1003. The bracket is very thin strip so that if a cover is used, it will not create an opening for heat and steam to escape. The device is suspending in fixed position with respect to the spa and its water 1002 that rises when bathers enter the spa and are detected via capacitance electrodes 1007 as described in US 2013/0313204. The module further incorporates an FC dispenser as described above using smaller cartridges (typically around 1" diameter) and a water pH balancing sodium hydroxide packaged in the film barrier packets 1010 in cartridge 1009 driven by rotating shaft 1011 driven by motor 1012 in the water tight enclosure 1013 and further controlled by the onboard electronics 1014 powered by battery pack 1015. In this configuration the gas generated by the warm water interaction with the trichlor when the FC dispenser is closed is vented to the outside via tube 1006 connecting the top of the FC dispenser to thin venting channel 1005 built into the strip hanger 1004 and thus avoids the accumulation of noxious gas under the spa cover which can further deteriorate the spa components.

In an alternative embodiment, the system utilizes a cartridge of dichlor with or without a pH modification cartridge since dichlor is more pH neutral. The dichlor is packaged in individual packets the water impermeable film strip as described above that are peeled or sliced or poked to allow the content to dispense to the spa water.

This system, or portions thereof, can be used in a spa in conjunction with other devices used to reduce water contamination such as ozonators, salt water chlorine generators, UV lamp sanitizers and turn them on only when they are needed. This extends their field life and reduces energy consumption. Ozone consumes chlorine so is best used when there is bather load to oxidize and not used when chlorine is providing a background disinfectant level in between soaks.

What is claimed is:

1. A water quality management system for a water installation containing water, the system comprising:
a water quality measurement module adapted to monitor water quality of the water in the water installation and to send water quality information to a controller, the water quality measurement module comprising a plurality of colorimetric test pads, each test pad enclosed in a water and vapor-proof barrier, a sensor adapted to sense a color change in a test pad for processing by the controller and a motor adapted to expose a test pad to water to permit water to reach the test pad;
a chemical dispensing module adapted to dispense chemicals directly into the water installation in response to signals from the controller based on the color change; and
a communication mechanism configured to provide communication among the controller, the water quality measurement module, the chemical dispensing module and a user.

2. The system of claim 1 wherein the water quality measurement module further comprises a water temperature sensor, the controller being configured to adjust chemical dispensing based on a water temperature signal from the water temperature sensor.

3. The system of claim 1 wherein the water quality measurement module further comprises an air temperature sensor, the controller being configured to adjust chemical dispensing based on an air temperature signal from the air temperature sensor.

4. The system of claim 1 wherein the water quality measurement module further comprises a hydrophone, the controller being configured to adjust chemical dispensing based on a sound signal from the hydrophone.

5. The system of claim 1 wherein the water quality measurement module comprises a water turbidity sensor, the controller being configured to adjust operation of a water pump based on a turbidity signal from the water turbidity sensor.

6. The system of claim 1 wherein the water quality measurement module further comprises an air humidity sensor, the controller being configured to adjust chemical dispensing based on a humidity signal from the humidity sensor.

7. The system of claim 1 wherein the water quality measurement module further comprises an accelerometer.

8. The system of claim 1 wherein the chemical dispensing module is adapted to float in the water.

9. The system of claim 1 wherein the chemical dispensing module is adapted to maintain orientation and buoyancy as chemicals are dispensed.

10. The system of claim 1 wherein the chemical dispensing module comprises a collapsible bladder containing a chemical to be dispensed into the water.

11. The system of claim 10 further comprising a chemical port communicating with the bladder and adapted to be underwater.

12. The system of claim 1 further comprising a vent adapted to vent gas generated by the chemicals.

13. The system of claim 1 wherein the chemical dispensing module comprises a quantity of the chemicals enclosed in a water-dissolvable package and disposed in a chemical chamber.

14. The system of claim 1 wherein the chemical dispensing module comprises a compartment arranged and configured to trap gases released by the chemicals.

15. The system of claim 14 wherein the controller is configured to activate an opening in the compartment to release the gases.

16. The system of claim 1 wherein the chemical dispensing module comprises a sensor adapted to sense depletion of at least one of the chemicals in the chemical dispensing module.

17. The system of claim 1 wherein the chemicals are disposed in doses sealed in waterproof packets, the chemical dispensing module comprising a motor configured to release a dose of chemicals from a packet.

18. The system of claim 1 further comprising a pump module adapted to control pumping of the water in response to signals from the controller.

19. A water quality measurement apparatus adapted to monitor water quality of a water installation, comprising:
   a plurality of colorimetric test pads, each test pad enclosed in a water and vapor-proof barrier film;
   a sensor adapted to sense a color change in a test pad; and
   a motor adapted to advance a test pad and to breach the barrier film to permit water to reach the test pad.

20. The apparatus of claim 19 wherein the water quality measurement apparatus further comprises a water temperature sensor.

21. The apparatus of claim 19 wherein the water quality measurement apparatus is adapted to float in water.

22. The apparatus of claim 19 further comprising a light source arranged and configured to illuminate a test pad of the plurality of test pads when the sensor senses a color change in the test pad.

23. The apparatus of claim 19 further comprising a disposable cartridge in which the plurality of colorimetric test pads is disposed.

24. The apparatus of claim 23 wherein the disposable cartridge is adapted to be attached to a buoyancy device.

25. The apparatus of claim 19 wherein the plurality of colorimetric test pads are arranged in a strip.

26. The apparatus of claim 19 further comprising a transmitter adapted to communicate information obtained by the sensor.

27. A water quality measurement apparatus adapted to monitor water quality of a water installation, comprising:
   a disposable cartridge adapted to connect to a buoyancy device;
   a plurality of colorimetric test pads disposed in the disposable cartridge, each test pad enclosed in a water and vapor-proof barrier film;
   a sensor disposed in the disposable cartridge and adapted to sense a color change in a test pad;
   a motor disposed in the disposable cartridge and adapted to advance a test pad and to breach the barrier film to permit water to reach the test pad; and
   a microprocessor disposed in the disposable cartridge and configured to control the motor and the sensor.

28. The apparatus of claim 27 further comprising a light source arranged and configured to illuminate a test pad of the plurality of test pads when the sensor senses a color change in the test pad.

29. The apparatus of claim 27 wherein the plurality of colorimetric test pads are arranged in a strip.

30. The apparatus of claim 27 further comprising a transmitter adapted to communicate information obtained by the sensor, the microprocessor being further configured to control the transmitter.

* * * * *